US012000849B2

(12) United States Patent
Makino et al.

(10) Patent No.: US 12,000,849 B2
(45) Date of Patent: Jun. 4, 2024

(54) AUTOMATIC ANALYZER

(71) Applicant: HITACHI HIGH-TECH CORPORATION, Tokyo (JP)

(72) Inventors: Akihisa Makino, Tokyo (JP); Hajime Yamazaki, Tokyo (JP); Keiko Yoshikawa, Tokyo (JP); Manabu Ando, Tokyo (JP); Masahiko Iijima, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 8 days.

(21) Appl. No.: 17/530,623

(22) Filed: Nov. 19, 2021

(65) Prior Publication Data

US 2022/0074959 A1 Mar. 10, 2022

Related U.S. Application Data

(63) Continuation of application No. 16/520,437, filed on Jul. 24, 2019, now Pat. No. 11,209,448, which is a
(Continued)

(30) Foreign Application Priority Data

Jun. 11, 2012 (JP) .................................. 2012-131492

(51) Int. Cl.
*G01N 35/02* (2006.01)
*G01N 21/11* (2006.01)
(Continued)

(52) U.S. Cl.
CPC ........... *G01N 35/025* (2013.01); *G01N 21/11* (2013.01); *G01N 21/82* (2013.01); *G01N 33/86* (2013.01);
(Continued)

(58) Field of Classification Search
None
See application file for complete search history.

(56) References Cited

U.S. PATENT DOCUMENTS 3,914,773 A * 10/1975 Harrower ........... G01N 33/4905
346/121
4,451,433 A 5/1984 Yamashita et al.
(Continued)

FOREIGN PATENT DOCUMENTS

CN 101213437 A 7/2008
JP 2000-321286 A 11/2000
(Continued)

OTHER PUBLICATIONS

Chinese Office Action received in corresponding Chinese Application No. 201380030385.X dated Jul. 17, 2015.
(Continued)

*Primary Examiner* — P. Kathryn Wright
(74) *Attorney, Agent, or Firm* — MATTINGLY & MALUR, PC

(57) ABSTRACT

A high-throughput automatic analyzer integrates a biochemical analysis section and a blood coagulation analysis section. The analyzer is capable of achieving a reduction in size, system cost, and lifecycle cost. The automatic analyzer includes: a reaction disk; a first reagent dispensing mechanism that dispenses a reagent to reaction cells on the reaction disk; a photometer that irradiates a reaction solution in the reaction cell with light; a reaction cell cleaning mechanism; a reaction vessel supply unit that supplies a disposable reaction vessel for mixing and reacting a sample and a reagent with each other; a second reagent dispensing mechanism that dispenses a reagent to the disposable reaction vessel; a blood coagulation time measuring section that irradiates a reaction solution in the disposable reaction vessel with light to detect transmitted or scattered light; and
(Continued)

a sample dispensing mechanism that dispenses a sample to the reaction cell and the disposable reaction vessel.

7 Claims, 15 Drawing Sheets

Related U.S. Application Data continuation of application No. 15/616,296, filed on Jun. 7, 2017, now Pat. No. 10,416,179, which is a continuation of application No. 14/402,906, filed as application No. PCT/JP2013/064428 on May 24, 2013, now Pat. No. 9,696,329.

(51) Int. Cl.
    *G01N 21/82*     (2006.01)
    *G01N 33/86*     (2006.01)
    *G01N 35/00*     (2006.01)
    *G01N 35/10*     (2006.01)
    *G01N 35/04*     (2006.01)

(52) U.S. Cl.
    CPC . *G01N 35/00584* (2013.01); *G01N 35/00693* (2013.01); *G01N 35/0092* (2013.01); *G01N 35/1004* (2013.01); *G01N 2021/115* (2013.01); *G01N 2035/00425* (2013.01); *G01N 2035/00673* (2013.01); *G01N 2035/0094* (2013.01); *G01N 2035/0097* (2013.01); *G01N 2035/0437* (2013.01); *G01N 2035/0453* (2013.01)

(56) References Cited

U.S. PATENT DOCUMENTS

| | | |
|---|---|---|
| 2007/0229830 A1 | 10/2007 | Yamamoto et al. |
| 2008/0044311 A1 | 2/2008 | Iguchi |
| 2008/0070318 A1* | 3/2008 | Yamamoto ....... G01N 35/00594 436/164 |
| 2008/0158552 A1 | 7/2008 | Tokunaga et al. |
| 2009/0137048 A1 | 5/2009 | Yamazaki et al. |
| 2011/0283779 A1 | 11/2011 | Wada et al. |
| 2012/0020838 A1 | 1/2012 | Mimura et al. |
| 2012/0039748 A1 | 2/2012 | Mimura et al. |
| 2012/0048036 A1 | 3/2012 | Mimura |
| 2019/0346470 A1 | 11/2019 | Makino et al. |

FOREIGN PATENT DOCUMENTS

| | | | |
|---|---|---|---|
| JP | 2001-013151 A | | 1/2001 |
| JP | 200561921 A | * | 3/2005 |
| JP | 2007-263911 A | | 10/2007 |
| JP | 2007280814 A | * | 10/2007 |
| JP | 2011-099681 A | | 5/2011 |
| JP | 2011-232249 W | | 11/2011 |
| JP | 2012-007923 W | | 1/2012 |
| WO | 2006/107016 A1 | | 10/2006 |
| WO | 2007/004466 A1 | | 1/2007 |
| WO | 2010/087137 A1 | | 8/2010 |
| WO | 2010/117044 A1 | | 10/2010 |
| WO | 2013/187210 A1 | | 12/2013 |

OTHER PUBLICATIONS

Extended European Search Report received in corresponding European Application No. 13804200.7 dated Feb. 8, 2016.
Machine-generated English translation of JP 2011-99681 To Yoshikawa et al., Published May 19, 2011.
Japanese Office Action received in corresponding Japanese Application No. 2020-131534 dated Jul. 6, 2021.

* cited by examiner

HEAT AND DISCHARGE REAGENT

MEASURE COAGULATION TIME

DISCHARGE CLEANING WATER OR CLEANING AGENT

HOLD DISPOSABLE REACTION VESSEL THAT HAS UNDERGONE COAGULATION TIME MEASUREMENT

FIG.4j

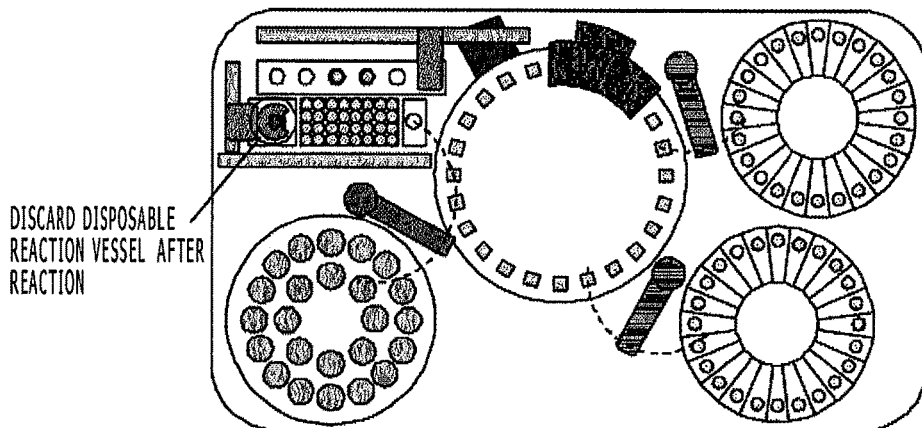

DISCARD DISPOSABLE REACTION VESSEL AFTER REACTION

FIG.5

COAGULATION TIME ITEMS OF SINGLE-REAGENT SYSTEM
(SINGLE-REAGENT SYSTEM FOR COAGULATION 1, COAGULATION 2, AND COAGULATION 3)

{MEASUREMENT REQUESTS} COAGULATION 1 -> COAGULATION 2 -> BIOCHEMICAL 1 -> BIOCHEMICAL 2 -> COAGULATION 3 -> BIOCHEMICAL 3 -> BIOCHEMICAL 4 -> BIOCHEMICAL 5 -> BIOCHEMICAL 6

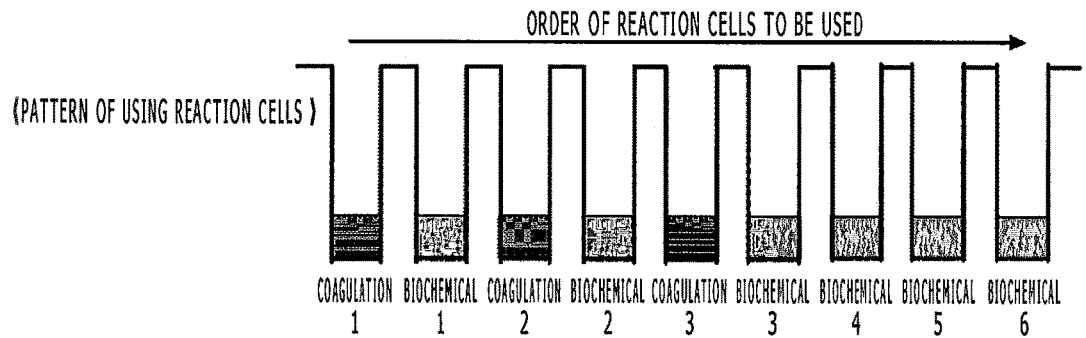

COAGULATION TIME ITEMS OF DOUBLE-REAGENT SYSTEM (DOUBLE-REAGENT SYSTEM FOR COAGULATION 1, THE FIRST REAGENT FOR COAGULATION 1a AND THE SECOND REAGENT FOR COAGULATION 1b; SINGLE-REAGENT SYSTEM FOR COAGULATION 2)

{MEASUREMENT REQUESTS} COAGULATION 1 -> BIOCHEMICAL 1 -> BIOCHEMICAL 2 -> COAGULATION 2 -> BIOCHEMICAL 3 -> BIOCHEMICAL 4 -> BIOCHEMICAL 5 -> BIOCHEMICAL 6

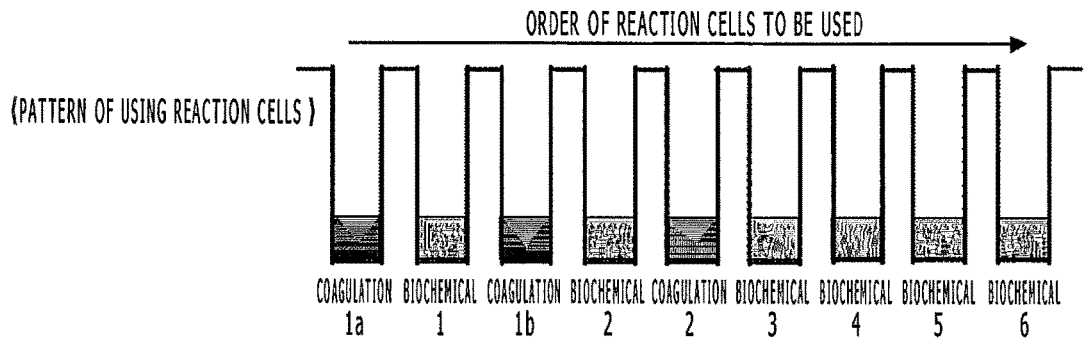

PICK UP MIXTURE SOLUTION

HEAT AND DISCHARGE MIXTURE SOLUTION

SECOND REAGENT TO COAGULATION REAGENT PICKUP POSITION AFTER PLURALITY OF CYCLES

FIG. 10
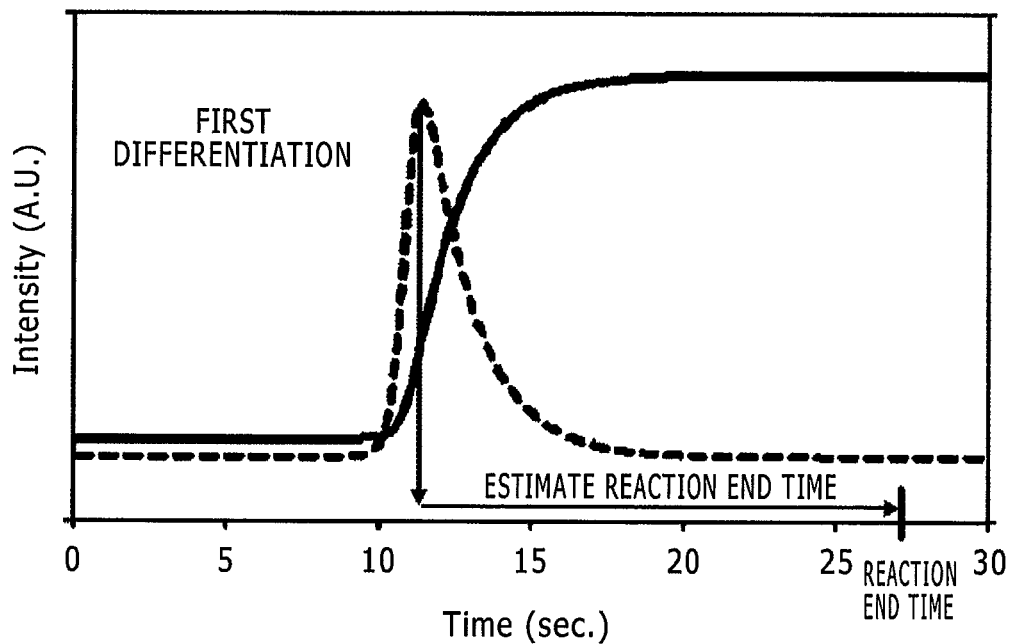
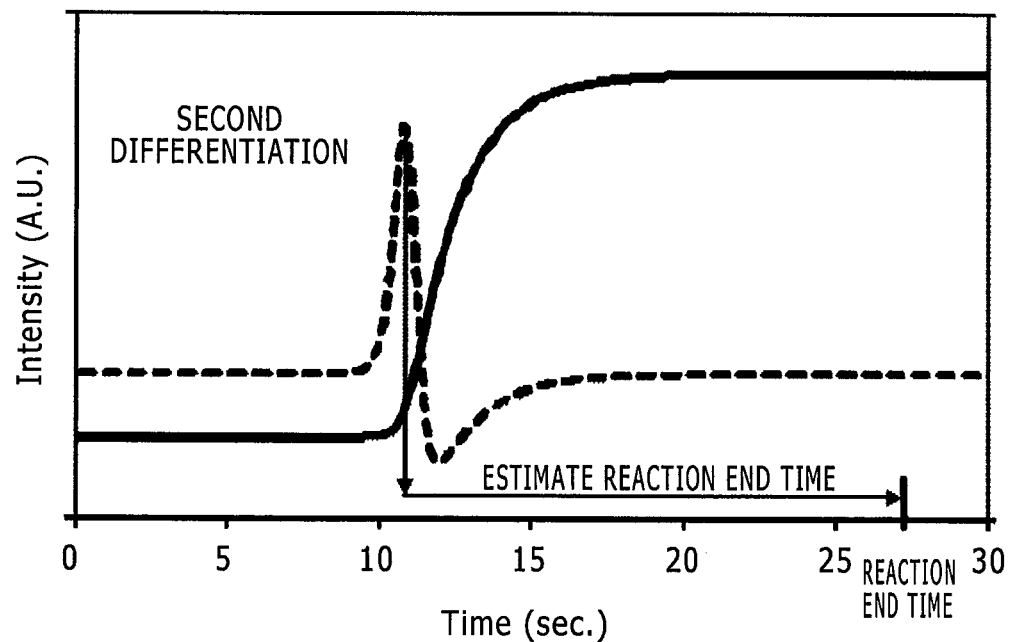

AUTOMATIC ANALYZER

TECHNICAL FIELD

The present invention relates generally to automatic analyzers that analyze amount of components contained in samples such as blood and urine and, more particularly, to an automatic analyzer capable of measuring biochemical analysis items and blood coagulation time items.

BACKGROUND ART

A known automatic analyzer designed to analyze amount of components contained in a sample irradiates a reaction solution, in which a sample and a reagent are mixed with each other, with light from a light source. The analyzer then measures the intensity of the obtained transmitted or scattered light with respect to a single wavelength or a plurality of wavelengths so as to determine the amount of a component on the basis of a relation between light intensity and concentration.

The automatic analyzer disclosed in patent document 1 includes a reaction disk that repeats rotation and stop, the reaction disk having optically transparent reaction cells arranged circumferentially thereon. While the reaction disk is rotating, a transmitted light measuring section disposed at a predetermined position in the automatic analyzer measures, for a period of approximately ten minutes, changes in the light intensity over time as a result of a reaction at predetermined time intervals (reaction process data). After the reaction, the reaction vessel is cleaned by a cleaning mechanism before being re-used for other analyses.

Two broad types of analysis fields exist for reactions of the reaction solution: specifically, a colorimetric analysis that uses a color reaction of a substrate and an enzyme; and a homogeneous immunoassay that uses an agglutination reaction by bonding of an antigen and an antibody. The immunoturbidimetric method and the latex coagulating method are known for the latter homogeneous immunoassay.

The immunoturbidimetric method uses a reagent containing an antibody to produce an immune complex with a substance to be measured (an antigen) contained in the sample. The immune complex is then optically detected to thereby determine component amount. The latex coagulating method uses a reagent that contains latex particles having an antibody sensitized (bonded) to their surfaces. The latex particles are agglutinated through an antigen-antibody reaction with the antigen contained in the sample. The agglutinated latex particles are then optically detected to thereby determine component amount. Analyzers performing even higher sensitive heterogeneous immunoassay are also known. These analyzers employ detection techniques by use of chemoluminescence and electrochemical luminescence and the B/F separation technique.

Patent document 2 discloses another automatic analyzer that measures coagulability of blood. Blood has fluidity inside the blood vessel; however, bleeding activates coagulation factors in the blood plasma and platelet in a chained manner, so that fibrinogen in the blood plasma turns to form fibrin, causing the bleeding to stop.

Blood coagulability may be exogenous where blood that escapes from the blood vessel coagulates, or endogenous where blood inside the blood vessel coagulates. Measurement items relating to the blood coagulability include prothrombin time (PT) as an exogenous blood coagulation reaction test and activated partial thromboplastin time (APTT) and a fibrinogen amount (Fbg) as an endogenous blood coagulation reaction test.

For each of these measurement items, a reagent that makes coagulation start is added to thereby cause deposition of fibrin and the resultant fibrin is detected with an optical, physical, or electrical technique. A known method employing the optical technique irradiates a reaction solution with light and identifies fibrin that deposits in the reaction solution as changes in intensity of scattered light or transmitted light over time, thereby calculating the time at which the fibrin starts deposition. In blood coagulation automatic analyzers represented by the automatic analyzer disclosed in patent document 2, blood coagulation reactions (Fbg item, in particular) feature a short coagulation time, as brief as several seconds, which requires that the intensity of light be measured at short intervals, that is, as short as approximately 0.1 seconds. Furthermore, once the reaction solution solidifies, the reaction vessel can no longer be re-used through cleaning. Specifically, the reaction is made at an independent photometric port and the reaction vessel is throwaway. The blood coagulation and fibrinolysis tests include measurement of coagulation factors and measurement of the coagulation-fibrinolysis marker, in addition to measurement of the blood coagulation time. The measurement of coagulation factors is taken mainly at a blood coagulation time measuring section. For the coagulation-fibrinolysis marker, analyses are made with the synthetic substrate method where a chromogenic synthetic substrate is used or the latex coagulating method mentioned earlier. Whereas the conventionally available PT, APTT, and Fbg are substantially fixed for the blood coagulation time items, the number of coagulation-fibrinolysis marker items are expected to increase to respond to requirements for early diagnosis and treatment for disseminated intravascular coagulation syndromes (DIC), including soluble fibrin monomer complex (SFMC) and plasmin-$\alpha$2-plasmin inhibitor (PIC), in addition to D dimer and fibrin fibrinogen degradation product (FDP). The need thus exists for improved throughput of the automatic analyzers. In the analyzer disclosed in patent document 2, however, the coagulation-fibrinolysis marker is measured at the photometric port at which transmitted light can be measured. In conventional blood coagulation analyzers, both the coagulation time and the coagulation-fibrinolysis marker are generally analyzed at a fixed photometric port.

PRIOR ART DOCUMENTS

Patent Documents

Patent Document 1: U.S. Pat. No. 4,451,433
Patent Document 2: JP-2000-321286-A
Patent Document 3: JP-2001-013151-A
Patent Document 4: WO2006/107016
Patent Document 5: JP-2011-099681-A

SUMMARY OF THE INVENTION

Problem to be Solved by the Invention

Combining a biochemical analyzer with a blood coagulation analyzer should offer advantages of, for example, improved sample management process and greater labor saving in system control. Simply combining the two, however, leads to a larger system configuration, higher system cost, and other problems that are not negligible.

Analysis time generally varies from ten minutes for biochemical items to three to seven minutes for coagulation time items and thus reduced processing capacity may result depending on the analysis time and the type of detector. Measurement of coagulation time normally takes approximately three minutes and the processing capacity can be maintained at a high level by discarding/supplying reaction vessels upon completion of the measurement. The synthetic substrate method and the latex coagulating method are typically a 10-minute reaction, taking longer time than coagulation time items do. Use of a conventional blood coagulation analyzer that includes a fixed port only for measuring these analysis items thus results in significantly lower processing capacity.

To solve these problems involved with the combination of analyzers, patent document 3 discloses an automatic analyzer that includes a linear belt conveyor-driven blood coagulation analysis section and a circular belt conveyor-driven biochemical analysis section. This configuration requires that, for an analysis of a biochemical item or a coagulation item, the reaction vessel be transferred onto the biochemical analysis section by way of the blood coagulation analysis section and the biochemical analysis section is estimated to have a processing capacity of 200 to 300 [tests/hour]. The capacity falls short of the processing capacity of the biochemical automatic analyzer disclosed in patent document 1 that boasts of 1000 [tests/hour].

The automatic analyzer disclosed in patent document 4 includes a linear belt conveyor-driven blood coagulation analysis section that can use common disposable reaction vessels and a biochemical analysis section including the disposable reaction vessels. The biochemical analysis section using the disposable reaction vessels is estimated to have a processing capacity of 200 to 300 [tests/hour] and it still seems difficult to improve the processing capacity by a large margin.

In the blood coagulation time measurement, the reaction starts in several seconds after the reagent has been discharged. The automatic analyzer disclosed in patent document 4 therefore includes a reagent dispensing mechanism having a reagent heating function in order to allow the temperature of the reaction solution to be kept at 37 degrees Celsius (° C.) immediately following the discharge of the reagent. It takes 10 to 20 seconds, however, before the reagent stored in a reagent refrigerator maintained typically at a temperature of 5° C. to 10° C. can be heated to an adequate temperature. This has been one of the factors contributing to a decline in processing capacity of the system.

To solve this problem, the technique disclosed in patent document 5 preheats the reagent at a turntable-type biochemical analysis section. The technique pertains to effective ways of shortening final reagent heating time by use of the reagent nozzle and stabilizing temperature control. Simply combining the biochemical analysis section with the coagulation analysis section does not, however, enables efficient use of the reaction cells of the biochemical analysis section, which leads to lower processing capacity of the system.

Since the biochemical analysis sections in patent documents 3 and 4 assume use of the disposable reaction vessels, using the disposable reaction vessels only for heating the reagent will increase the consumable cost. From the viewpoint of lifecycle cost, adoption of the biochemical analysis sections in patent documents 3 and 4 has been virtually impractical.

Means for Solving the Problem

In some aspects, the present invention provides the following.

(1) An automatic analyzer includes: a reaction disk having a reaction cell arranged circumferentially thereon, the reaction cell mixing and reacting a sample and a reagent with each other, the reaction disk repeating rotation and stop; a first reagent dispensing mechanism that dispenses a reagent to the reaction cell; a photometer that irradiates a reaction solution in the reaction cell with light to thereby detect light; a reaction cell cleaning mechanism that cleans the reaction cell; a reaction vessel supply unit that supplies a disposable reaction vessel for mixing and reacting a sample and a reagent with each other; a second reagent dispensing mechanism with a reagent heating function that dispenses a reagent to the disposable reaction vessel; a blood coagulation time measuring section that irradiates a reaction solution in the disposable reaction vessel with light to thereby detect transmitted light or scattered light; and a sample dispensing mechanism that dispenses a sample to the reaction cell and the disposable reaction vessel.

The automatic analyzer, including the sample dispensing mechanism that dispenses a sample to the reaction cell and the disposable reaction vessel, can be built more compactly than that including dedicated sample dispensing mechanisms for both the reaction cell and the disposable reaction vessel. In addition, system cost and lifecycle cost can also be prevented from increasing. Moreover, a single system can achieve both biochemical analysis and blood coagulation analysis, so that a high-throughput automatic analyzer can be provided.

(2) The automatic analyzer of (1) above further includes a controller that controls the blood coagulation time measuring section so that one cycle time in an analysis operation cycle of the blood coagulation time measuring section is a multiple of n (n being a natural number) of one cycle time in an analysis operation cycle of the reaction disk.

The foregoing arrangement allows a biochemical analyzer to perform blood coagulation time measurement without involving a major reduction in its throughput even with a blood coagulation time measuring section newly added thereto. For example, when n is 2 or more, a timing at which the blood coagulation time measuring section performs an analysis operation falls on a timing at which a biochemical analysis operation starts at all times, so that there will be no waste of time. Thus, a high-throughput automatic analyzer can be provided.

(3) In the automatic analyzer of (1) or (2), control is performed such that, at a timing at which a sample is dispensed to the blood coagulation time measuring section, the reaction disk is rotated without the sample being dispensed to the reaction cell to thereby produce an empty reaction cell and a reagent for measuring blood coagulation time is discharged into the empty reaction cell with the use of the first reagent dispensing mechanism before being preheated.

This allows an empty reaction cell inevitably produced in the blood coagulation time measurement to be used for preheating the reagent for measuring blood coagulation time, enabling an efficient use of the reaction cells. A high-throughput automatic analyzer can thus be provided.

Advantage of the Invention

An object of the present invention is to provide a high-throughput automatic analyzer that integrates a biochemical analysis section and a blood coagulation analysis section, and is capable of achieving a reduction in size, system cost, and lifecycle cost.

BRIEF DESCRIPTION OF DRAWINGS

FIG. 4j is a diagram showing a general mechanical operation in blood coagulation time measurement (single-reagent system) according to the embodiment of the present invention.

FIG. 5 is a diagram showing an exemplary pattern of using the reaction cells with respect to an analysis request for biochemical items and blood coagulation time items according to the embodiment of the present invention.

FIG. 10 is a diagram illustrating a method of estimating coagulation reaction end time according to an embodiment of the present invention.

MODES FOR CARRYING OUT THE INVENTION

Figure 1:
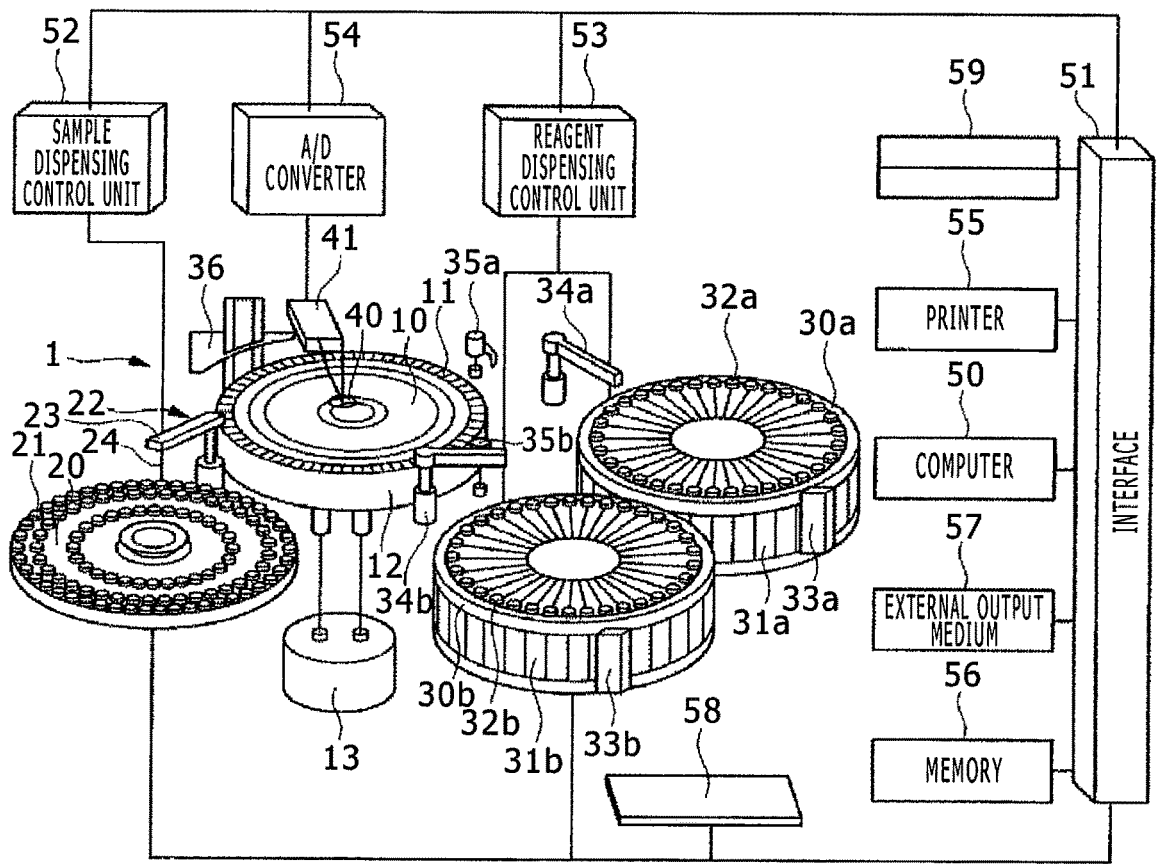
FIG. 1 is a system block diagram showing a general configuration of a turntable-type automatic analyzer that assumes a base of an embodiment of the present invention.

An embodiment of the present invention will be described in detail below with reference to the accompanying figures. In all the drawings for describing the embodiment, like or corresponding parts are identified by the same reference numerals and descriptions for those parts will be omitted wherever feasible.

In this description, analysis items for which only a first reagent is used are referred to as a single-reagent system and analysis items for which both the first reagent and a second reagent are used are referred to as a double-reagent system.

FIG. 1 is a system block diagram showing a general configuration of a turntable-type automatic analyzer that assumes a base of an embodiment of the present invention. As shown in FIG. 1, this automatic analyzer 1 mainly includes a reaction disk 10, a sample disk 20, a first reagent disk 30a, a second reagent disk 30b, a light source 40, a photometer 41, and a computer 50.

The reaction disk 10 is capable of intermittent rotation, and a plurality of reaction cells 11 formed of a translucent material is mounted on the reaction disk 10 along a circumferential direction thereof. The reaction cells 11 are maintained at a predetermined temperature (for example, at 37° C.) by means of a constant-temperature bath 12. A temperature of a fluid inside the constant-temperature bath 12 is adjusted with a constant-temperature maintaining device 13.

The sample disk 20 has a plurality of sample vessels 21 mounted thereon in two rows extending in the circumferential direction in the example shown in FIG. 1, each of the sample vessels 21 containing therein a biological sample such as blood and urine. A sample dispensing mechanism 22 is disposed near the sample disk 20. The sample dispensing mechanism 22 mainly includes a movable arm 23 and a pipette nozzle 24 attached to the movable arm 23. The sample dispensing mechanism 22, through the foregoing arrangements, causes the movable arm 23 to move the pipette nozzle 24 to an appropriate dispensing position during a dispensing sequence and causes the pipette nozzle 24 to pick up a predetermined amount of sample from a sample vessel 21 located at a pickup position in the sample disk 20 and to discharge the sample into a reaction cell 11 at a discharge position on the reaction disk 10.

The first reagent disk 30a and the second reagent disk 30b are disposed inside a first reagent refrigerator 31a and a second reagent refrigerator 31b, respectively. The first reagent refrigerator 31a and the second reagent refrigerator 31b respectively contain a plurality of first reagent bottles 32a and a plurality of second reagent bottles 32b respectively placed in a circumferential direction of the first reagent disk 30a and the second reagent disk 30b. The first reagent bottles 32a and the second reagent bottles 32b are each affixed with a label that indicates reagent identification information, such as a bar code. The first reagent bottles 32a and the second reagent bottles 32b each store therein a reagent solution that is associated with an analysis item to be analyzed by the automatic analyzer 1. Additionally, the first reagent refrigerator 31a and the second reagent refrigerator 31b are provided as an adjunct with a first bar code reader 33a and a second bar code reader 33b, respectively. The first bar code reader 33a and the second bar code reader 33b read the bar codes indicated on outer walls of the first reagent bottles 32a and the second reagent bottles 32b during reagent registration. The read reagent information is registered in a memory 56, together with a specific position on the first reagent disk 30a or the second reagent disk 30b.

A first reagent dispensing mechanism 34a and a third reagent dispensing mechanism 34b, each having a mechanism substantially identical to that of the sample dispensing mechanism 22, are disposed near the first reagent disk 30a and the second reagent disk 30b, respectively. During the reagent dispensing, a pipette nozzle included in each of the first reagent dispensing mechanism 34a and the third reagent dispensing mechanism 34b sucks the reagent from the first reagent bottle 32a or the second reagent bottle 32b that is associated with the analysis item and positioned at a reagent receiving position on the reaction disk 10. The pipette nozzle then discharges the reagent into a corresponding reaction cell 11.

A first agitating mechanism 35a and a second agitating mechanism 35b are disposed in an area surrounded by the reaction disk 10, the first reagent disk 30a, the second reagent disk 30b, the first reagent dispensing mechanism 34a, and the third reagent dispensing mechanism 34b. The first reagent dispensing mechanism 34a or the third reagent dispensing mechanism 34b agitates a mixture solution of the sample and the reagent stored in the reaction cell 11 to thereby promote reaction.

The light source 40 is disposed at a position near a center of the reaction disk 10 and the photometer 41 is disposed on an outer peripheral side of the reaction disk 10. A row of the reaction cells 11 that have been subjected to the agitation is rotationally moved so as to pass through a photometric position between the light source 40 and the photometer 41. The light source 40 and the photometer 41 constitute an optical detection system. The photometer 41 detects transmitted light or scattered light.

A reaction solution of the sample and the reagent in each of the reaction cells 11 are subjected to a photometric process each time the reaction solution passes through the photometer 41 during rotation of the reaction disk 10. An analog signal of the scattered light measured for each sample is applied to an analog-to-digital (A/D) converter 54. An inside of a used reaction cell 11 is cleaned by a reaction cell cleaning mechanism 36 disposed near the reaction disk 10 to enable repeated use of the reaction cells 11.

A control system and a signal processing system in the automatic analyzer 1 will now be described with reference to FIG. 1. The computer 50 is connected to a sample dispensing control unit 52, a reagent dispensing control unit 53, and the A/D converter 54 via an interface 51. The computer 50 sends a command to the sample dispensing control unit 52 to thereby control a sample dispensing operation. The computer 50 also sends a command to the reagent dispensing control unit 53 to thereby control a reagent dispensing operation. Additionally, the computer 50 reads a measured value in the form of a digital signal as converted by the A/D converter 54.

A printer 55 for printing, the memory 56 and an external output medium 57 serving as storages, a keyboard 58 for inputting, for example, an operational command, and a CRT display (display device) 59 for displaying a screen are connected to the interface 51. The display device 59 may be a liquid crystal display, in addition to the CRT display. The memory 56 may include a hard disk memory or an external memory. The memory 56 stores therein information such as passwords of operators, display levels of different screens, analysis parameters, analysis item requests, calibration results, and analyses.

The following describes how the automatic analyzer 1 shown in FIG. 1 analyzes samples. Analysis parameters relating to the items to be analyzed by the automatic analyzer 1 are previously input via an information inputting device, such as the keyboard 58, and stored in the memory 56. The operator selects a test item requested for each sample using an operational function screen.

At this time, information such as a patient ID is also input from the keyboard 58. To analyze the test item specified for each sample, the pipette nozzle 24 of the sample dispensing mechanism 22 dispenses a predetermined amount of the sample from the sample vessel 21 to the reaction cell 11 in accordance with the analysis parameter.

The reaction cell 11 into which the sample has been dispensed is transferred through the rotation of the reaction disk 10 and stops at the reagent receiving position. The pipette nozzles of the first reagent dispensing mechanism 34a and the third reagent dispensing mechanism 34b dispense a predetermined amount of the reagent solution to the reaction cell 11 in accordance with the analysis parameter of the corresponding test item. The order in which the sample and the reagent are dispensed may be opposite to this example; that is, the reagent may first be dispensed before the sample.

The sample and the reagent are thereafter agitated and mixed by the first agitating mechanism 35a and the second agitating mechanism 35b. When the reaction cell 11 passes through the photometric position, the photometer 41 measures the transmitted light or the scattered light of the reaction solution. The measured transmitted light or scattered light is translated to a corresponding numerical value that is proportional to light intensity by means of the A/D converter 54 and the numerical value is fetched by the computer 50 via the interface 51.

Concentration data is calculated using this converted numerical value and on the basis of a calibration curve previously measured with an analysis method specified for each test item. The component concentration data as a result of the analysis of each test item is output to the printer 55 or a screen of the CRT display 59.

Prior to the performance of the above-described measurement, the operator sets various parameters and registers the samples, as required for the analysis measurement, via the operational screen of the CRT display 59. In addition, the operator checks analyses obtained after the measurement using the operational screen on the CRT display 59.

Figure 2:
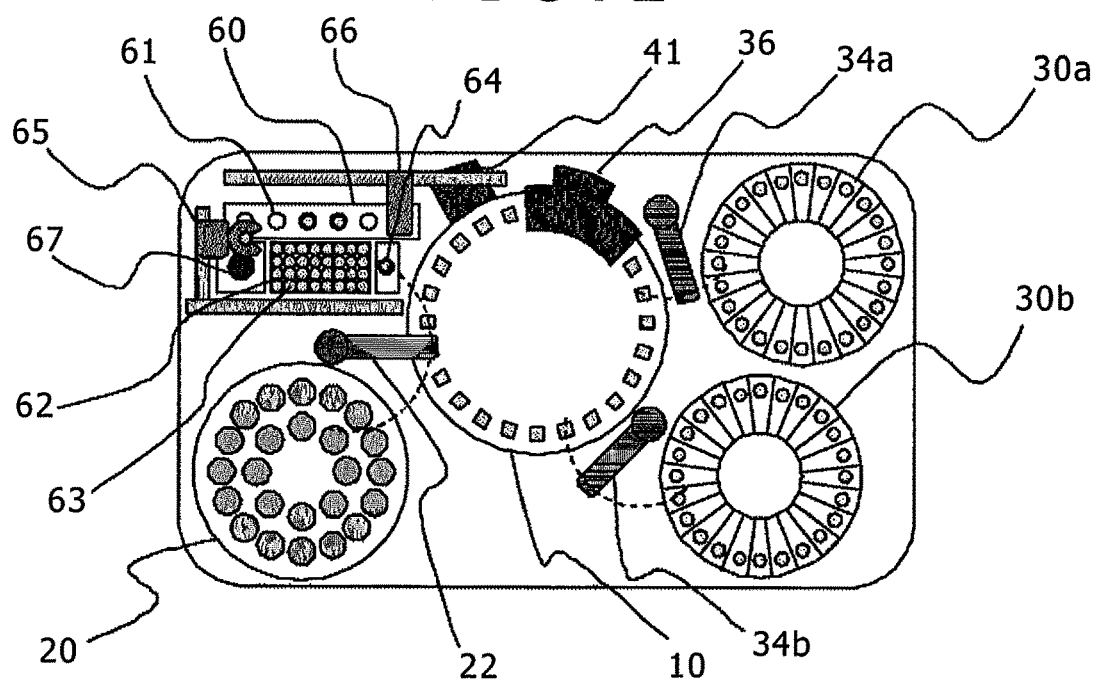
FIG. 2 is a schematic diagram showing an automatic analyzer including a turntable-type biochemical analysis section and a blood coagulation time measuring section according to an embodiment of the present invention.

FIG. 2 is a schematic diagram showing an automatic analyzer including a turntable-type biochemical analysis section and a blood coagulation time measuring section according to an embodiment of the present invention. The automatic analyzer shown in FIG. 2 includes a sample dispensing mechanism 22 shared between the turntable-type biochemical analysis section and the blood coagulation time measuring section. Compared to the turntable-type biochemical automatic analyzer shown in FIG. 1, the automatic analyzer shown in FIG. 2 additionally includes a reaction vessel supply unit 63 keeping a stock of a plurality of disposable reaction vessels 62, a reaction vessel temperature-regulating block 60 including a plurality of coagulation time detecting parts 61, a reaction vessel transfer mechanism 65 transferring the disposable reaction vessels 62, a second reagent dispensing mechanism with a reagent heating function 66, a coagulation time sample dispensing position 64, and a reaction vessel discard section 67.

Figure 3:
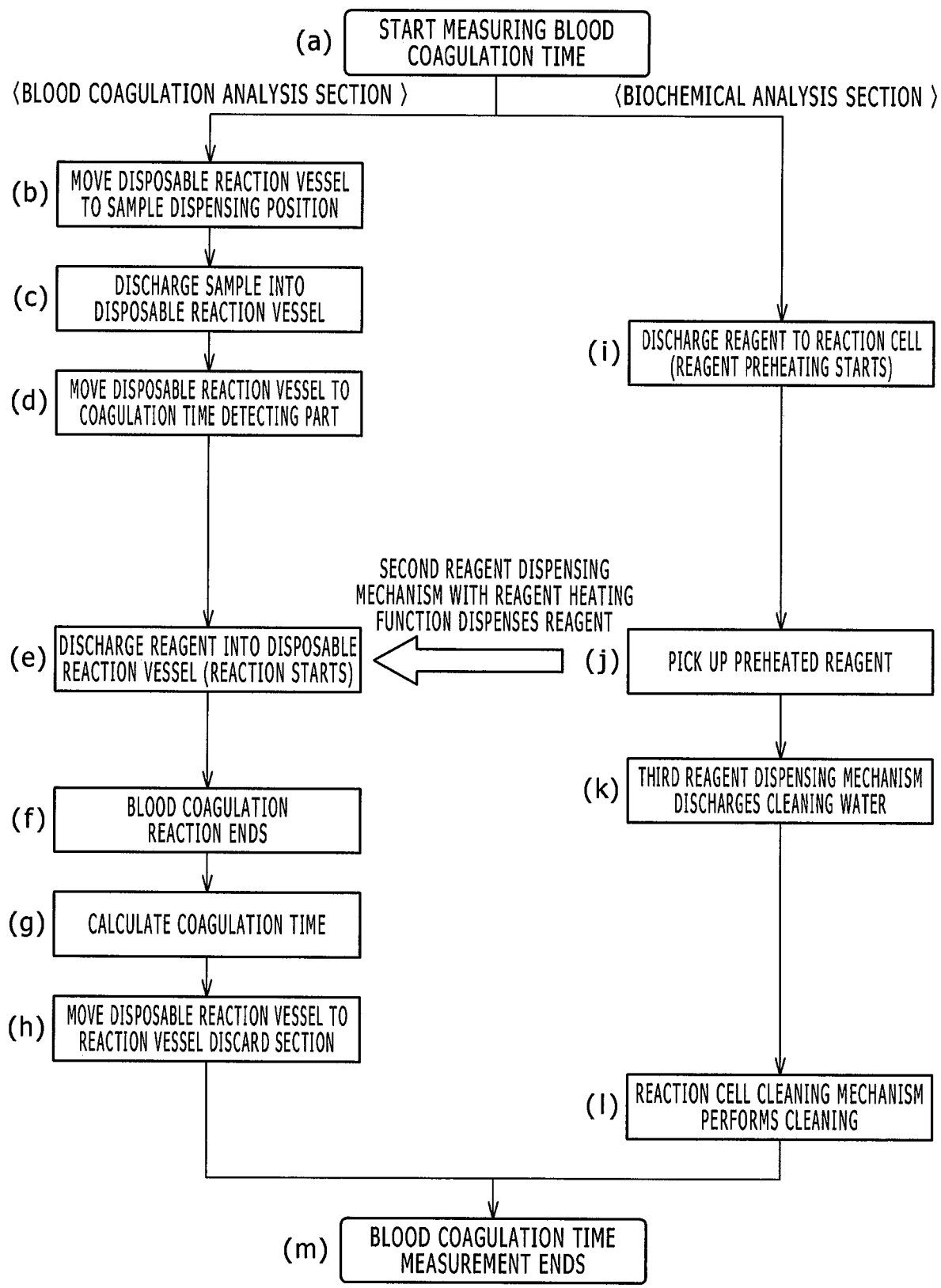
FIG. 3 is an exemplary diagram showing a blood coagulation time measurement sequence for a single-reagent system according to the embodiment of the present invention.

FIG. 3 is an exemplary diagram showing a blood coagulation time measurement sequence for the single-reagent system according to the embodiment of the present invention. The sample discharged to the disposable reaction vessel 62 is heated by the coagulation time detecting parts 61 included in the reaction vessel temperature-regulating block 60 of a blood coagulation analysis section (b to d) and the reagent is preheated (to 37° C.) at the reaction cell 11 on the reaction disk 10 of the biochemical analysis section (i to j). The reagent preheated to 37° C. is further heated by the second reagent dispensing mechanism with a reagent heating function 66 (to, for example, 40° C.) and discharged into the disposable reaction vessel 62 that contains therein the sample heated to 37° C. in advance, whereby a blood coagulation reaction is started (e). After the reaction (f), coagulation time is calculated (g) and the disposable reaction vessel 62 is discarded at the reaction vessel discard section 67 (h). The first reagent dispensing mechanism 34a or the third reagent dispensing mechanism 34b discharges cleaning water or a cleaning agent into the reaction cell 11 from which the preheated reagent has been sucked (k). And the reaction cell 11 is thereafter cleaned by the reaction cell cleaning mechanism 36 (l).

Figure 4A:
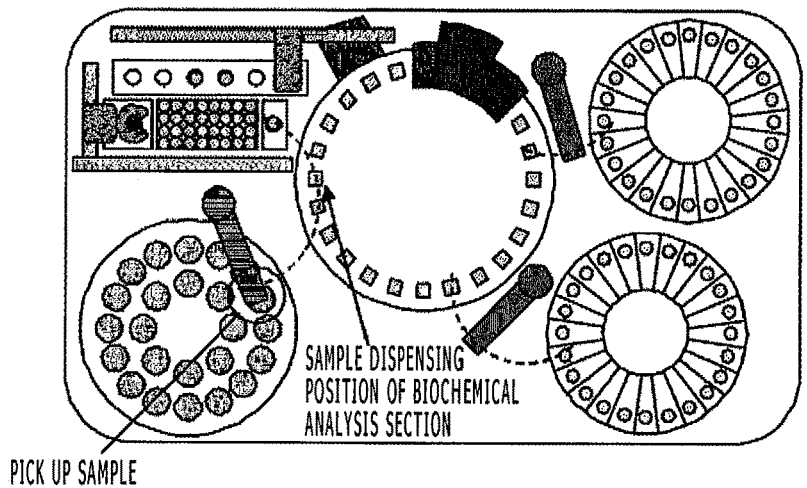
FIG. 4a is a diagram showing a general mechanical operation in blood coagulation time measurement (single-reagent system) according to the embodiment of the present invention.
Figure 4B:
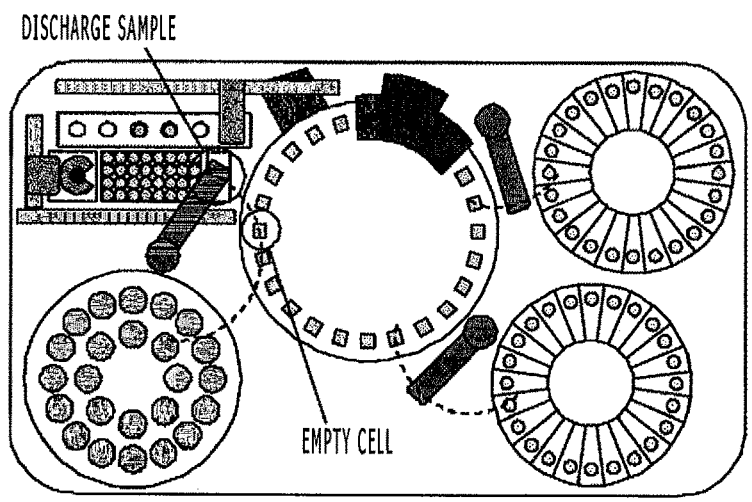
FIG. 4b is a diagram showing a general mechanical operation in blood coagulation time measurement (single-reagent system) according to the embodiment of the present invention.
Figure 4C:
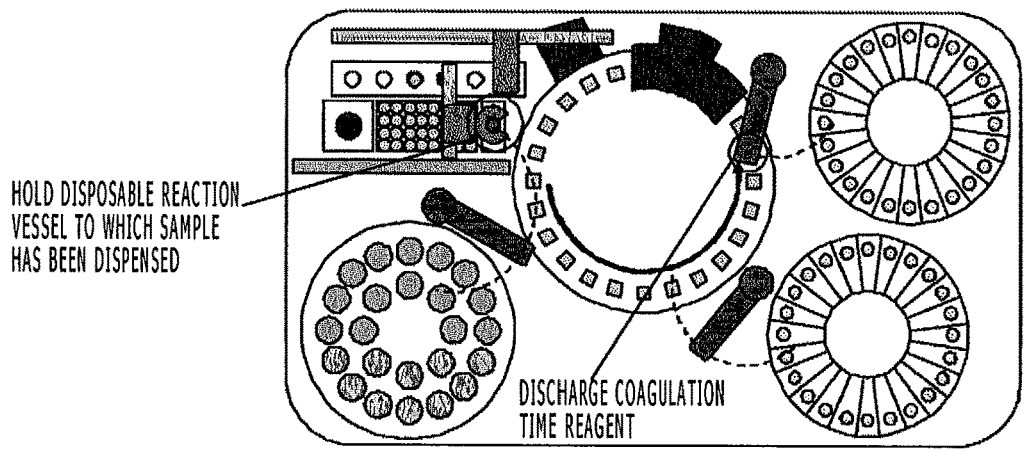
FIG. 4c is a diagram showing a general mechanical operation in blood coagulation time measurement (single-reagent system) according to the embodiment of the present invention.
Figure 4D:
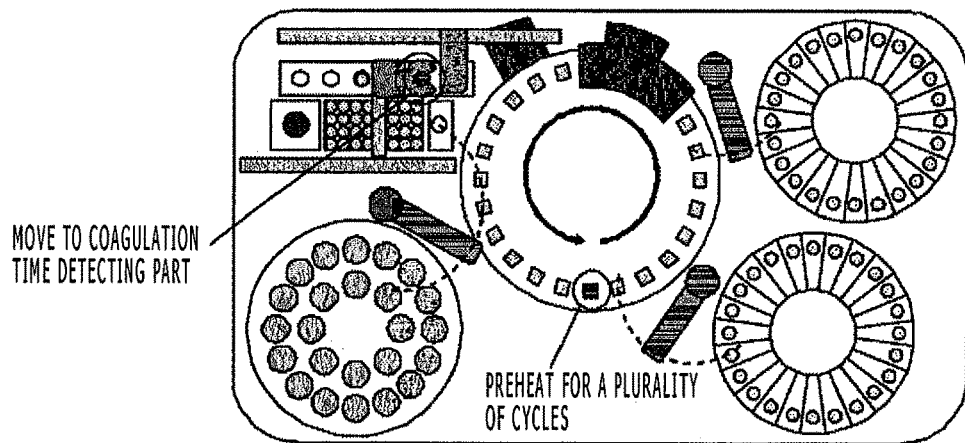
FIG. 4d is a diagram showing a general mechanical operation in blood coagulation time measurement (single-reagent system) according to the embodiment of the present invention.
Figure 4E:
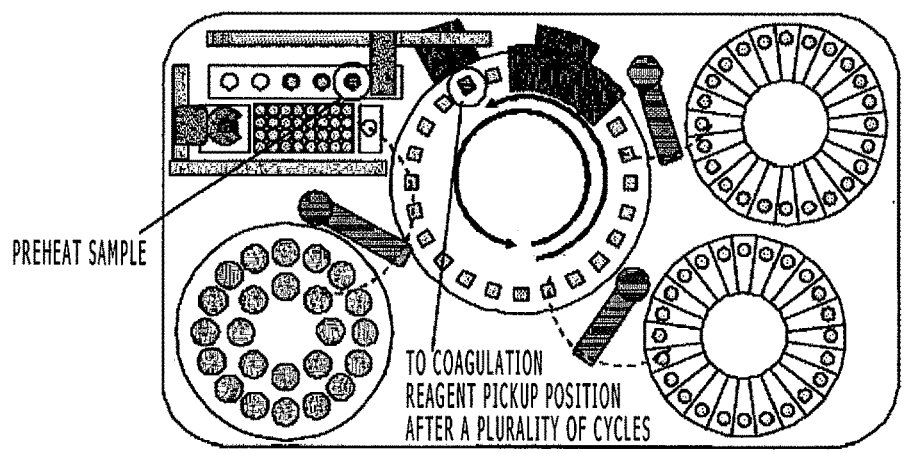
FIG. 4e is a diagram showing a general mechanical operation in blood coagulation time measurement (single-reagent system) according to the embodiment of the present invention.
Figure 4F:
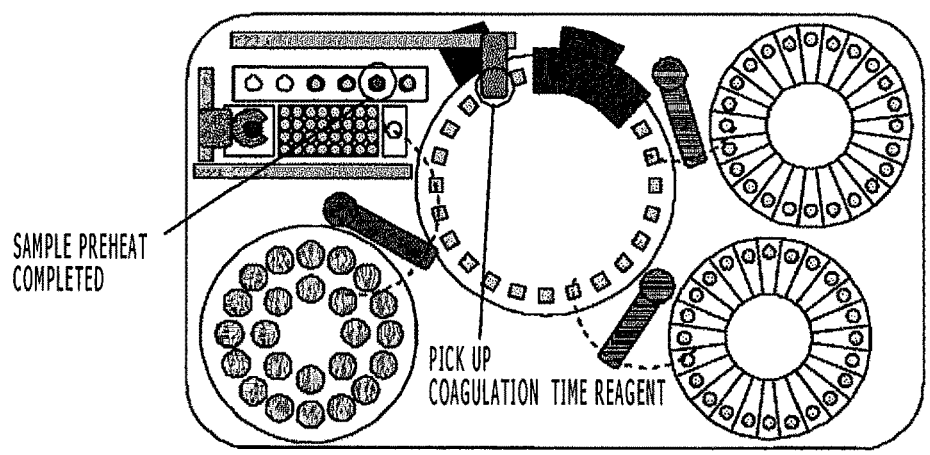
FIG. 4f is a diagram showing a general mechanical operation in blood coagulation time measurement (single-reagent system) according to the embodiment of the present invention.
Figure 4G:
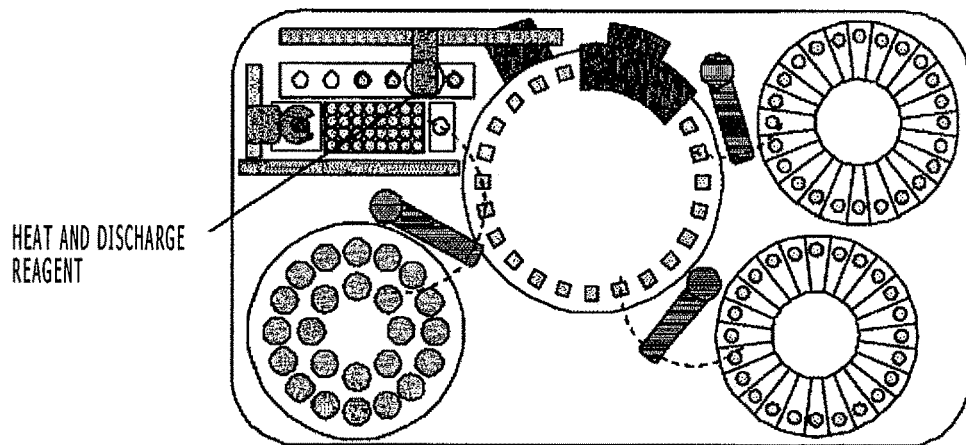
FIG. 4g is a diagram showing a general mechanical operation in blood coagulation time measurement (single-reagent system) according to the embodiment of the present invention.
Figure 4H:
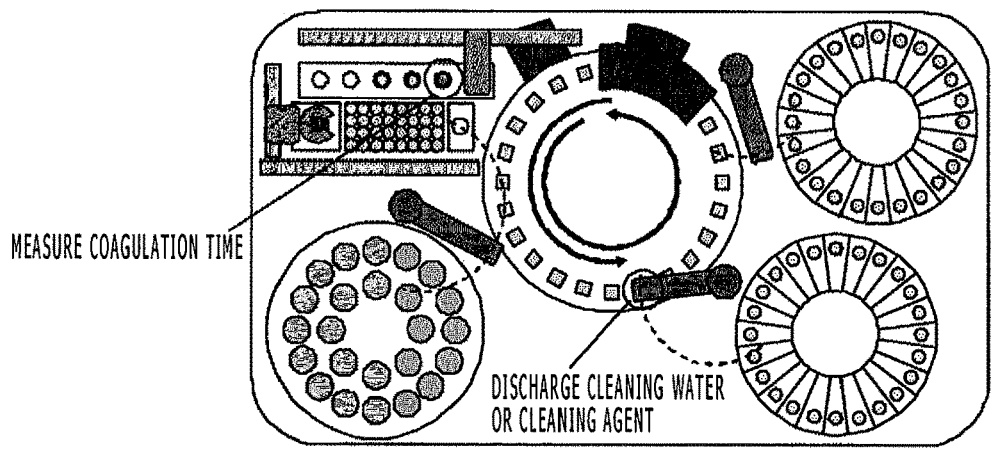
FIG. 4h is a diagram showing a general mechanical operation in blood coagulation time measurement (single-reagent system) according to the embodiment of the present invention.
Figure 4I:
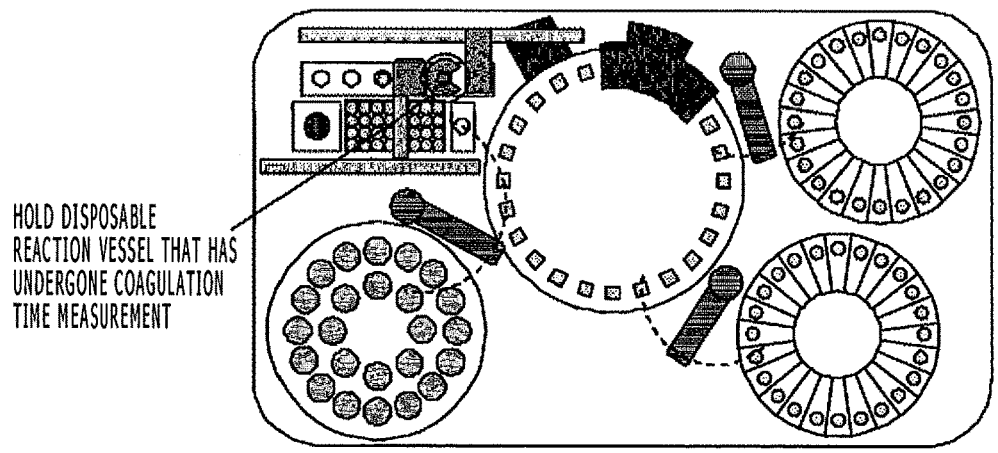
FIG. 4i is a diagram showing a general mechanical operation in blood coagulation time measurement (single-reagent system) according to the embodiment of the present invention.

A general mechanical operation in blood coagulation time measurement (the single-reagent system) will now be described with reference to FIGS. 4a to 4j. FIG. 4a shows that the reaction vessel transfer mechanism 65 has already moved the disposable reaction vessel 62 from the reaction vessel supply unit 63 to the coagulation time sample dispensing position 64, from which status the blood coagulation time measurement is started. The sample sucked by the sample dispensing mechanism 22 passes through the sample dispensing position in the biochemical analysis section and is dispensed to the disposable reaction vessel 62 at the coagulation time sample dispensing position 64 (FIGS. 4a and 4b). At this time, an empty reaction cell 11 not to be used for the analysis is produced at the reaction disk 10 (FIG. 4b). The disposable reaction vessel 62 to which the sample has been dispensed is transferred by the reaction vessel transfer mechanism 65 onto the coagulation time detecting part 61 included in the reaction vessel temperature-regulating block 60 and the sample is heated to 37° C. (FIGS. 4c and 4d). Meanwhile, the first reagent dispensing mechanism 34a dispenses the reagent for measuring blood coagulation time to the empty reaction cell 11 which is then preheated to 37° C. over a plurality of cycles (FIGS. 4c and 4d). The number of cycles for the preheating is set in advance in accordance with the time required by the reaction vessel temperature-regulating block 60 to heat the sample. The reagent that has been completely preheated is positioned at a blood coagulation reagent pickup position and sucked by the second reagent dispensing mechanism with a reagent heating function 66 (FIGS. 4e and 4f). The reagent for measuring blood coagulation time is first heated by the second reagent dispensing mechanism with a reagent heating function 66 to a predetermined required temperature (e.g., 40° C.) so as to have a temperature of 37° C. immediately after the discharge. The reagent is thereafter discharged into the disposable reaction vessel 62 that contains therein the sample (FIG. 4g). At this time, a spurt of the reagent being discharged agitates the sample and the reagent and a sequence to measure the blood coagulation time starts (FIG. 4h). The disposable reaction vessel 62 that has been subjected to the blood coagulation time measurement is discarded to the reaction vessel discard section 67 by the reaction vessel transfer mechanism 65 (FIGS. 4i and 4j).

As described above, the reaction disk is rotated without the sample being dispensed thereto to thereby produce an empty reaction cell at a timing at which the sample is dispensed to the blood coagulation time measuring section. The first reagent dispensing mechanism 34a is then employed to discharge the reagent for measuring blood coagulation time into the empty reaction cell and the reagent for measuring blood coagulation time is preheated. This control procedure enables use of the empty reaction cell inevitably produced in the blood coagulation time measurement for preheating the reagent for measuring blood coagulation time, thus achieving an efficient use of the reaction cells. An automatic analyzer offering a high throughput can thus be provided. It is also known that the reagent is mounted on the reagent disk and is transferred from the reagent disk to the blood coagulation time measuring section by way of the reaction disk. In setting the system, the foregoing configuration eliminates the need for a new cold insulation container for the reagent for measuring blood coagulation time and for a reagent dispensing mechanism requiring a long distance travel, so that an increase in system cost can be minimized.

The first reagent dispensing mechanism 34a or the third reagent dispensing mechanism 34b discharges, after several cycles, cleaning water or the cleaning agent into the reaction cell 11 from which the preheated reagent for measuring blood coagulation time has been sucked. The reaction cell 11 is cleaned, after another several cycles, by the reaction cell cleaning mechanism 36 (FIG. 4g).

Preferably, the first reagent dispensing mechanism 34a that dispenses the reagent for measuring blood coagulation time is a reagent dispensing mechanism that dispenses the first reagent in the biochemical analysis section. The first reagent is discharged into the reaction vessel at a cycle close to a timing at which the sample is dispensed. The first reagent dispensing mechanism 34a is disposed so as to achieve the foregoing purpose. Thus, there is no need to change the conventional turntable-type driving method when dispensing the reagent for measuring blood coagulation time. In addition, the reagent dispensing mechanism can be shared between the biochemical analysis section and the blood coagulation time measuring section, so that further reduction in size can be achieved.

The third reagent dispensing mechanism 34b that dispenses the cleaning water or the cleaning agent into the reaction cell 11 from which the reagent for measuring blood coagulation time has been sucked may be identical to the first reagent dispensing mechanism 34a. In the biochemical analysis section, however, the third reagent dispensing mechanism 34b preferably dispenses the second reagent. The second reagent is discharged after the first reagent has been discharged into the reaction cell. And the third reagent dispensing mechanism 34b is disposed so as to achieve this operation. This disposition eliminates the need for changing the conventional turntable-type driving method in order to clean the reaction cell that stores therein the reagent for measuring blood coagulation time. Additionally, the reagent dispensing mechanism can be shared between the biochemical analysis section and the blood coagulation time measuring section, so that further reduction in size can be achieved.

The reaction disk repeats a cycle of rotating a predetermined rotational angle and stopping. It is therefore preferable that the second reagent dispensing mechanism 66 be disposed in consideration of its dispensing position such that a specific reaction cell visits in sequence a dispensing position of the first reagent dispensing mechanism 34a, that of the second reagent dispensing mechanism 66, and that of the third reagent dispensing mechanism 34b. This is because of the following reason: specifically, the cleaning by the reaction cell cleaning mechanism 36 can be achieved at an identical number of cycles with reference to the dispensing of the reagent for measuring blood coagulation time and the dispensing of the first reagent, so that a higher throughput can be promoted.

FIG. 5 shows an exemplary pattern of using the reaction cells 11 on the reaction disk 10 with respect to an analysis request for biochemical items and blood coagulation time items according to the embodiment of the present invention. In FIG. 5, one cycle time in an analysis operation cycle of the blood coagulation time measuring section is twice as long as one cycle time in an analysis operation cycle of the biochemical analysis section. As described with reference to FIGS. 4a to 4j, the blood coagulation time measuring section is required to perform such an operation as the transfer of the disposable reaction vessel within the one-cycle time. Thus, the one-cycle time in the analysis operation of the blood coagulation time measuring section may preferably be longer than the one-cycle time in the analysis operation of the biochemical analysis section. The fact is, however, not as simple as the idea that the one-cycle time only has to be longer. Specifically, the one cycle time in the analysis operation of the blood coagulation time measuring section is longer by a multiple of a natural number than the one-cycle time in the analysis operation of the biochemical analysis section so that a timing at which the blood coagulation time measuring section performs the analysis operation coincides with a timing at which the biochemical analysis section starts to perform the analysis operation at all times.

Assume that measurement requests are made as shown in the upper diagram in FIG. 5 with respect to the coagulation time items for the single-reagent system. The upper diagram in FIG. 5 shows that measurement requests for coagulation 1 and coagulation 2 occur consecutively. Because the one-cycle time in the analysis operation of the blood coagulation time measuring section is double the one-cycle time in the analysis operation of the biochemical analysis section as described above, the use of the reaction cells in the order of the measurement requests will disable processing performed by the blood coagulation time measuring section that requires twice as long one cycle time as that of the biochemical analysis section. Take, for instance, 4 seconds and 8 seconds. Whereas the reaction disk makes one rotation and one stop in 4 seconds, the reaction vessel supply unit 63 that keeps a stock of a plurality of disposable reaction vessels 62 to be used for measurement, the reaction vessel transfer mechanism 65 that transfers the disposable reaction vessels 62, and the second reagent dispensing mechanism with a reagent heating function 66 are controlled to be driven at a cycle of 8 seconds. In the example shown in the upper diagram of FIG. 5, therefore, the order of the reaction cells to be used is controlled to be changed so that the blood coagulation time measurement for coagulation 1 can be performed at a cycle of 8 seconds by inserting biochemical 1 between coagulation 1 and coagulation 2. As is known from the above, the reaction cells 11 are to be alternately used for reagent preheating even when coagulation time items are consecutively requested. Suppose that the one-cycle time in the analysis operation cycle of the blood coagulation time measuring section is n-fold and coagulation time items are consecutively requested. Control is then performed to change the order of the reaction cells to be used such that n−1 biochemical analysis items are inserted.

Assume that measurement requests are made as shown in the lower diagram in FIG. 5 with respect to the coagulation time items for the double-reagent system. The measurement requests include coagulation 1 of the double-reagent system. While the need is to independently preheat two reagents of coagulation 1a and coagulation 1b and move the two reagents to the disposable reaction vessel, because of the twice as long one-cycle time involved, the blood coagulation time measuring section is unable to perform processing if reaction cells are used consecutively for coagulation 1a and coagulation 1b. Control is therefore performed such that, in addition to one extra empty reaction cell being provided per sample for these two reagents, one extra empty reaction cell is provided and the order of reaction cells is changed so that, instead of providing empty reaction vessels consecutively, biochemical 1 immediately following coagulation 1 is moved up and coagulation 1a and coagulation 1b alternate with each other. Specifically, although a timing has arrived at which biochemical 2 is dispensable, one cycle is waited for the reaction cell for coagulation 1b without dispensing the sample for biochemical 2 therein. This control enables efficient processing even when reagents in the single-reagent system and in the double-reagent system are mixed with other. With the n-fold one-cycle time, control is performed to change the order of the reaction cells to be used such that n−1 biochemical analysis items are inserted between coagulation 1a and coagulation 1b.

Even with a mixture of events of the upper and lower diagrams, control is performed to change the order of the reaction cells to be used for the n-fold one-cycle time such that n−1 biochemical analysis items are inserted between reaction cells containing a coagulation reagent. Understandably, however, n−1 cycles are to be waited for the absence of a request for biochemical analysis measurement. The control performed in FIG. 5 is performed by, for example, a controller included in the computer 50 shown in FIG. 1.

Figure 6:
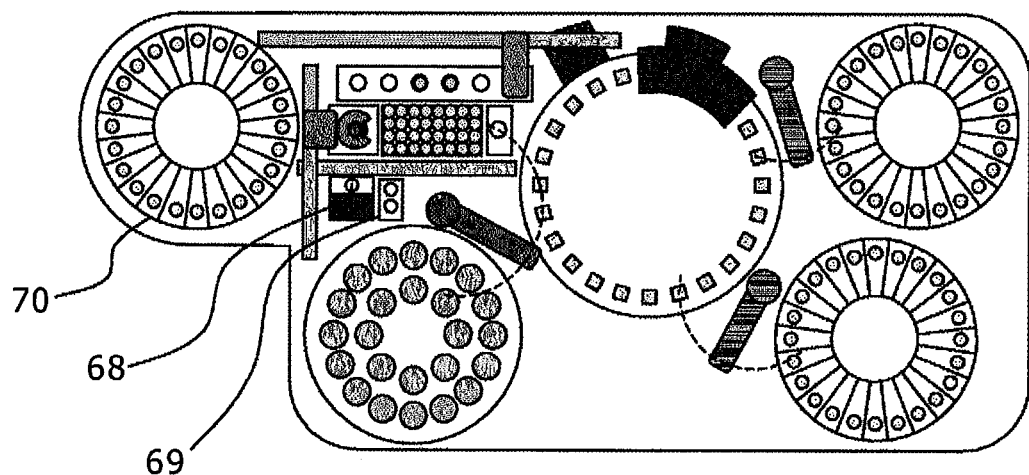
FIG. 6 is a schematic diagram showing an automatic analyzer that includes a biochemical analysis section, a blood coagulation time measuring section, and a heterogeneous immunoassay section according to an embodiment of the present invention.

FIG. 6 is a schematic diagram showing an automatic analyzer that includes a biochemical analysis section, a blood coagulation time measuring section, and a heterogeneous immunoassay section according to an embodiment of the present invention. A detecting section of heterogeneous immunoassay 68 for heterogeneous immunoassay item measurement and a B/F separating mechanism 69 are disposed in an operable range of the reaction vessel transfer mechanism 65. The disposable reaction vessels 62, the reaction vessel temperature-regulating block 60, the reaction vessel transfer mechanism 65, the reaction vessel supply unit 63, and the reaction vessel discard section 67 are shared with the blood coagulation time measuring section. An automatic analyzer offering an even greater number of enhanced functions can thus be configured through the addition of minimum essential mechanisms. It is to be noted that, in FIG. 6, a disk of reagent of heterogeneous immunoassay 70 is added in an operable range of the second reagent dispensing mechanism with a reagent heating function 66. The configuration of this embodiment can provide a high-throughput automatic analyzer with a short TAT that integrates a biochemical analysis section, a blood coagulation analysis section, and an analysis section of heterogeneous immunoassay, while achieving a reduction in size, system cost, and lifecycle cost.

The operation described with reference to FIG. 5 was that, for the analysis items of both the single-reagent system and the double-reagent system, the sample dispensing mechanism is used to dispense the sample in the disposable reaction vessel before either the first reagent or the first reagent and the second reagent are preheated in the reaction cell. The following describes another example in which the sample for the analysis items of the single-reagent system is dispensed to the disposable reaction vessel with the use of the sample dispensing mechanism, and the sample for the analysis items of the double-reagent system is dispensed to the reaction cell with the use of the sample dispensing mechanism. An exemplary analysis item of the single-reagent system includes prothrombin time (PT) and an exemplary analysis item of the double-reagent system includes activated partial thromboplastin time (APTT). For a fibrinogen amount (Fbg), the first reagent being a diluted solution is, however, treated as the double-reagent system. While FIGS. 3, 4a to 4i, and the upper diagram of FIG. 5 show the measurement sequence for the single-reagent system, FIGS. 7 to 9l show the measurement sequence for the double-reagent system.

Figure 7:
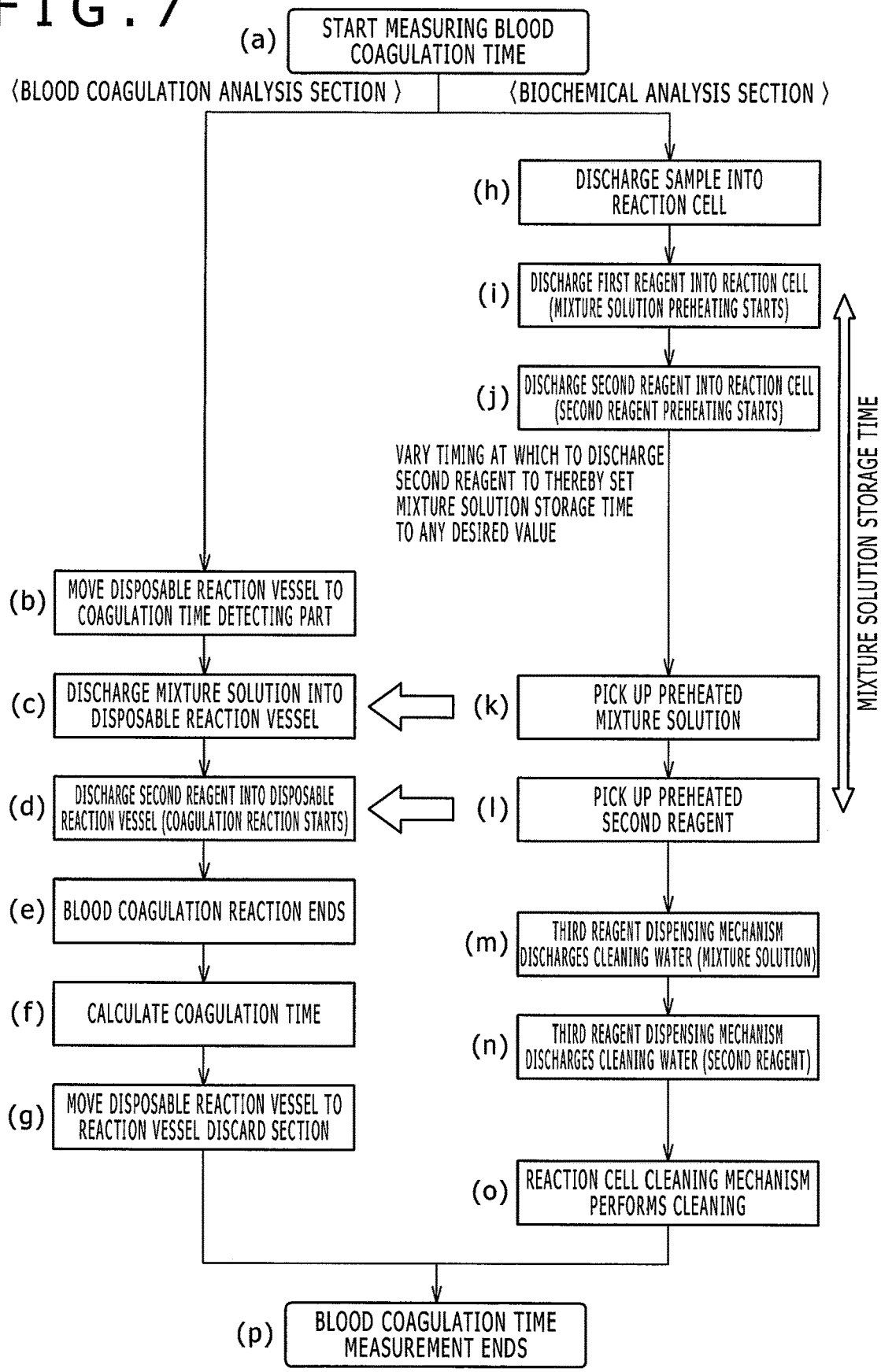
FIG. 7 is an exemplary diagram showing a blood coagulation time measurement sequence for a double-reagent system according to the embodiment of the present invention.

FIG. 7 is an exemplary diagram showing a blood coagulation time measurement sequence for the double-reagent system according to the embodiment of the present invention. In this example, the sample dispensing control unit 52 controls the sample dispensing mechanism in accordance with the analysis item measured at the blood coagulation time measuring section: specifically, the sample dispensing mechanism is controlled so as to dispense the sample to the disposable reaction vessel when the analysis item is associated with the single-reagent system and to dispense the sample to the reaction cell when the analysis item is associated with the double-reagent system.

After the sample is dispensed to a reaction cell 11, the first reagent dispensing mechanism 34a discharges a first reagent or a diluted solution to the reaction cell 11, so that preheating is started of a mixture solution of either the sample and the first reagent or the sample and the diluted solution (h to i). Moreover, after a predetermined number of cycles, the first reagent dispensing mechanism 34a discharges a second reagent to a second reaction cell 11 and preheating is started (j).

A disposable reaction vessel 62 is moved to a coagulation time detecting part 61 included in the reaction vessel temperature-regulating block 60 of the blood coagulation analysis section (b). The mixture solution and the second reagent preheated to 37° C. in the reaction cell 11 on the reaction disk 10 of the biochemical analysis section are each sucked by the second reagent dispensing mechanism with reagent heating function 66 (k to l) and are further heated (to, for example, 40° C.) before being discharged to the disposable reaction vessel 62 (c to d). These operations will make a blood coagulation reaction start. After the reaction is completed (e), the coagulation time is calculated (f) and the disposable reaction vessel 62 is discarded in the reaction vessel discard section 67 (g).

Thus, in the blood coagulation time measurement sequence for the double-reagent system shown in FIG. 7, the sample dispensing mechanism 22 dispenses the sample to the reaction cell and the first reagent dispensing mechanism 34a dispenses the first reagent or the diluted solution to the reaction cell; after the resultant mixture solution is stored in the reaction cell for a predetermined period of time, the second reagent dispensing mechanism with reagent heating function 66 dispenses the mixture solution in the disposable reaction vessel. The second reaction cell that contains therein the reagent (the second reagent) for starting the blood coagulation reaction to be discharged into the disposable reaction cell is provided separately from the reaction cell that contains therein the mixture solution. The sample dispensing control unit 52 controls the sample dispensing mechanism so that the reaction disk is rotated without the sample being dispensed to the second reaction cell to thereby make the second reaction cell an empty reaction cell. This control results in the reagent (the second reagent) for starting the blood coagulation reaction being discharged into the empty second reaction cell. The discharge allows the mixture solution, in addition to the second reagent, to be preheated.

The first reagent dispensing mechanism 34a or the third reagent dispensing mechanism 34b discharges the cleaning water or the cleaning agent into the reaction cell 11 from which the preheated mixture solution or second reagent has been sucked (m to n). The reaction cell 11 is thereafter cleaned by the reaction cell cleaning mechanism 36 (o).

The timing at which to dispense the second reagent can be set to any value with resolution of the operating cycle for each analysis item. This allows storage time to be efficiently allotted without changing the conventional driving method of the turntable type in such items as APTT requiring time for activation or pre-treatment by use of the first reagent. Specifically, it is preferable the time be varied in accordance with the analysis item by changing a timing at which to provide an empty cell for storing the second reagent on the basis of the analysis item, the time being required for the reagent (the second reagent) for starting the blood coagulation reaction to be discharged into the mixture solution after the mixture solution has been mixed. To keep the system control simple, it is preferable a period of time be set that begins when the first reagent dispensing mechanism discharges the second reagent and ends when the second reagent dispensing mechanism discharges the second reagent. In such a case, a timing at which to provide an empty cell for the second reagent after the sample has been discharged into the reaction cell may be determined uniformly regardless of the analysis item. Meanwhile, some analysis items have ideal time to add the second reagent after the sample and the first reagent have been mixed with each other. Thus, preferably, the time to add the second reagent is adjusted in accordance with the analysis item by varying the timing at which to provide the empty cell for storing the second reagent after dispensing of the sample in accordance with the analysis item.

Figure 8:
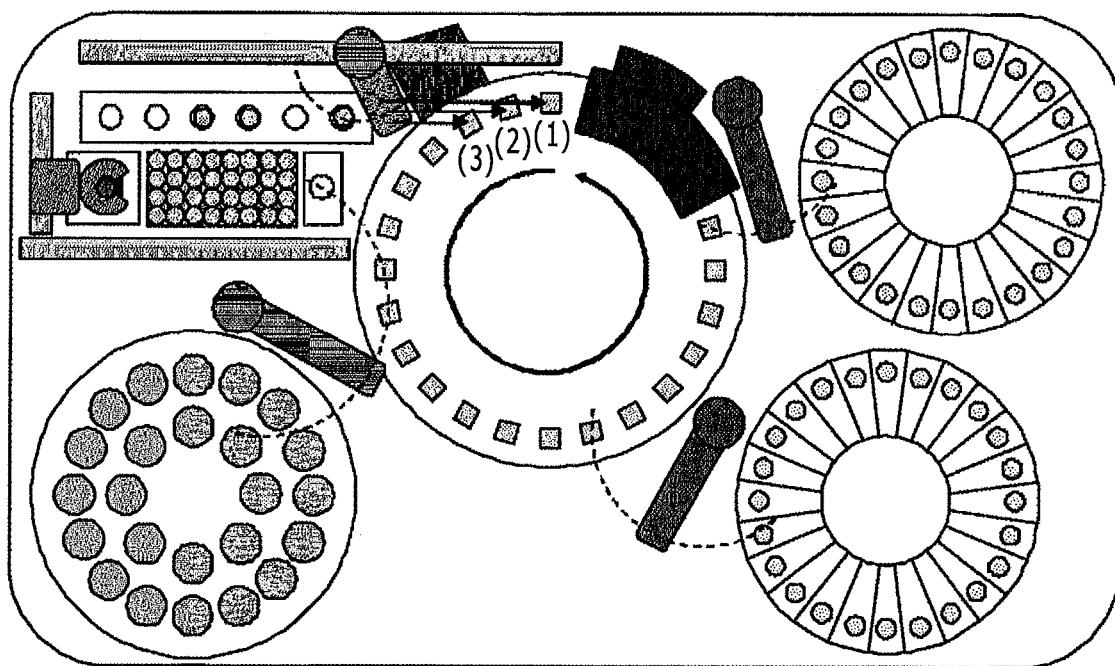
FIG. 8 is a diagram illustrating an embodiment of the present invention in which a pickup position of a second reagent dispensing mechanism with a reagent heating function is changed in accordance with storage time of a reagent or a mixture solution.

FIG. 8 shows a modification of the second reagent dispensing mechanism. The second reagent dispensing mechanism described above sucks a liquid from a single place on the reaction disk. FIG. 8 illustrates an exemplary second reagent dispensing mechanism capable of dispensing a liquid from reaction cells disposed at different positions on the reaction disk. As shown in FIG. 8, the second reagent dispensing mechanism with a reagent heating function 66 is capable of being positioned at a plurality positions (1) to (3) on the reaction disk 10 to thereby possibly allot time for activation or pre-treatment by use of the first reagent based on the pickup position. Additionally, the foregoing method may even be employed for controlling the storage time depending on the amount of mixture solution or reagent to make up for the time required for the preheating becoming longer with the increase in the amount of liquid to be preheated. It is therefore preferable that the dispensing position be varied in accordance with the type of liquid or the amount to be dispensed by making the second reagent dispensing mechanism capable of dispensing from reaction cells disposed at different positions. While the example shown in FIG. 8 illustrates that the second reagent dispensing mechanism is capable of dispensing a liquid from three positions, the number of positions from which to dispense a liquid may be two, four or more.

Figure 9A:
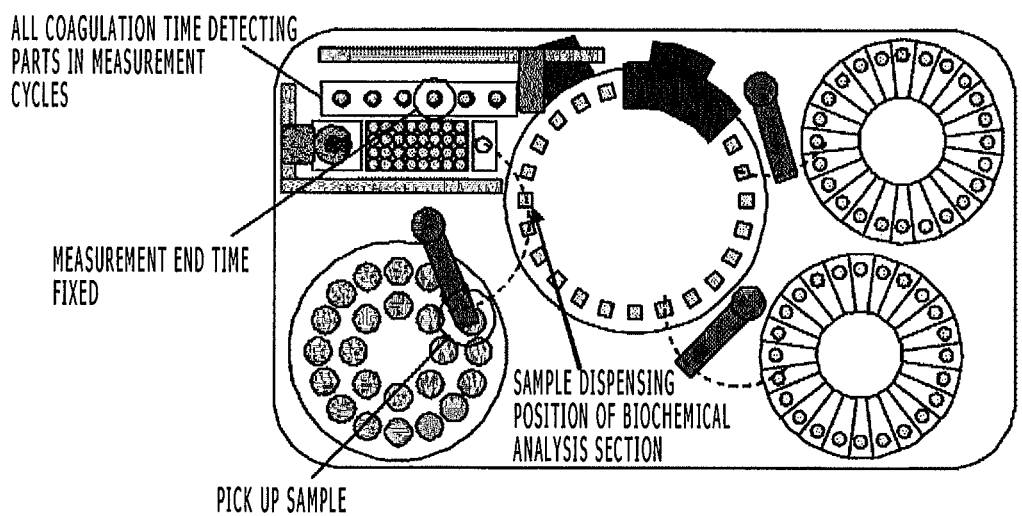
FIG. 9a is a diagram showing a general mechanical operation in blood coagulation time measurement (double-reagent system) according to the embodiment of the present invention.
Figure 9B:
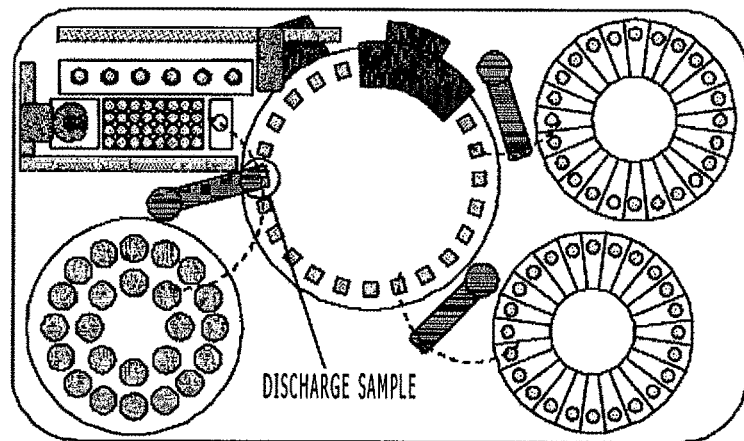
FIG. 9b is a diagram showing a general mechanical operation in blood coagulation time measurement (double-reagent system) according to the embodiment of the present invention.

The following describes with reference to FIGS. 9a to 9l a general mechanical operation in blood coagulation time measurement in the double-reagent system in an embodiment of the present invention. FIG. 9a, though indicating that all coagulation time detecting parts 61 are in measurement cycles, shows a condition in which measurement end time is fixed at one of the coagulation time detecting parts 61. When the analysis item is associated with the double-reagent system, the sample dispensing mechanism 22 sucks a sample at this time and dispenses the sample in a reaction cell 11 (FIG. 9b). The starting of sample dispensing for the double-reagent system upon the fixing of the measurement end time as described above shortens wait time to enable an efficient analysis, so that an automatic analyzer with a high throughput can be provided. A predetermined period of time is required before the sample is dispensed to the disposable reaction vessel after the sample has been dispensed to the reaction cell. This allows the sample to be dispensed to the reaction cell even when all coagulation time detecting parts 61 are occupied. Alternatively, as a method of shortening the wait time, it is also effective to start the sample dispensing for the double-reagent system on the basis of the maximum measurement time. For example, with the maximum measurement time set to 300 seconds, the disposable reaction vessel with which the measurement time elapses 300 seconds is set to be discarded regardless of whether the measurement end time is fixed. Assume that it takes 60 seconds to discharge the mixture solution to the disposable reaction vessel after the sample has been discharged to the reaction cell [(h) to (k) and (c) in FIG. 7]. It is then effective as a method of shortening the wait time to perform the sample dispensing with reference to 240 seconds that are obtained by subtracting 60 seconds from 300 seconds.

One possible method of fixing the measurement end time is to estimate reaction end time on the basis of a peak of results of differentiation of the reaction process. FIG. 10 illustrates this method. In FIG. 10, the abscissa represents time and the ordinate represents light intensity. FIG. 10 shows reaction process data curves (solid lines) of measurements obtained from the coagulation time detecting parts 61 and further shows results of differentiation of the reaction curves (broken lines). The upper diagram of FIG. 10 shows results of first differentiation, while the lower diagram of FIG. 10 shows results of second differentiation. Approximate reaction end time can be estimated from the peak of the results of either differentiation. Thus, the reaction end time is estimated on the basis of the peak time of the results of differentiation to thereby determine the reaction end time before the estimated time elapses. This enables the use of the peak time of the results of differentiation as reference for the start of sample dispensing.

As described above, preferably, the blood coagulation time measuring section includes a plurality of coagulation time detecting parts 61 on which the disposable reaction vessels are placed; if all coagulation time detecting parts 61 are occupied by the disposable reaction vessels, the blood coagulation time measuring section schedules items for dispensing samples in the reaction cells on the basis of a point in time at which the measurement end time is fixed with reference to a predetermined reaction end criterion or predetermined maximum measurement time; the blood coagulation time measuring section thereby dispenses a sample associated with the scheduled item to the reaction cell with all the coagulation time detecting parts 61 occupied. The reaction end criterion can be established on the basis of the peak time of the results of differentiation of the reaction process data curve as the measurements obtained from the coagulation time detecting parts.

Figure 9C:
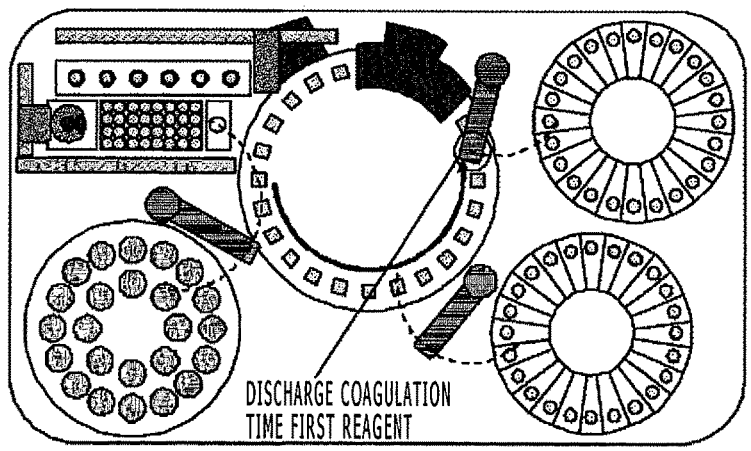
FIG. 9c is a diagram showing a general mechanical operation in blood coagulation time measurement (double-reagent system) according to the embodiment of the present invention.

Reference is made back to FIGS. 9a to 9l for the general operation. The first reagent dispensing mechanism 34a discharges the first reagent or the diluted solution into the reaction cell 11 in which the sample has been dispensed (FIG. 9c). The sample and the first reagent or the diluted solution may be agitated by means of a spurt of the reagent being discharged or the first agitating mechanism 35a not shown. The agitation by the first agitating mechanism 35a is likely to promote and stabilize the reaction. The mixture solution of the sample and the first reagent or the diluted solution is preheated to 37° C. on the reaction disk 10. During this time, a reference value relating to an amount of an interfering substance in the sample can be calculated through measurement of transmitted light or scattered light taken by the photometer 41. Specifically, the reference value relating to the amount of the interfering substance contained in the sample can be calculated while the mixture solution is stored in the reaction cell.

To measure absorbance of the mixture solution of the sample and the first reagent or the diluted solution using the photometer 41, degrees of turbidity, hemolysis, and yellow color are calculated with absorbance values of 480 nm, 505 nm, 570 nm, 600 nm, 660 nm, and 700 nm on the basis of the following expressions.

Turbidity $(L)=(1/C)\times$(difference in absorbance between 660 nm and 700 nm)

Hemolysis $(H)=(1/A)\times$(difference in absorbance between 570 nm and 600 nm$-B\times$difference in absorbance between 660 nm and 700 nm)

Yellowness $(I)=(1/D)\times$(difference in absorbance between 480 nm and 505 nm$-E\times$difference in absorbance between 570 nm and 600 nm)$-F\times$ difference in absorbance between 660 nm and 700 nm)

where C, A, and D are: Coefficients for outputting absorbance as serum information B, E, and F are: Coefficients for correcting an overlap of absorption spectrum Furthermore, measurements taken with the disposable reaction vessel can be corrected on the basis of the reference value relating to the amount of the interfering substance. For example, a correlation between this reference value and the light intensity in coagulation time measurement may be obtained to thereby correct the coagulation time measurements.

Figure 11:
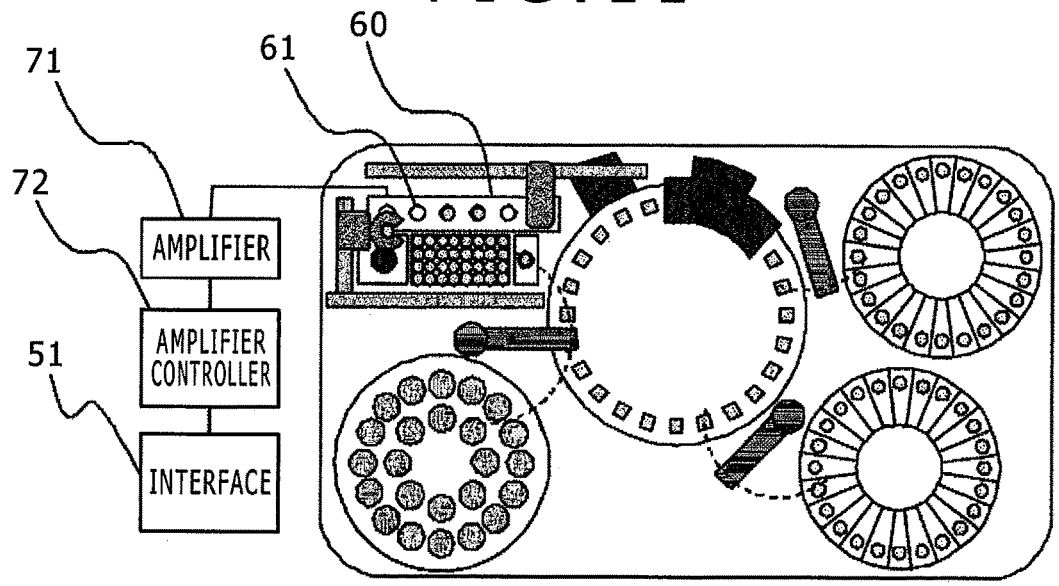
FIG. 11 is a schematic diagram showing an automatic analyzer that includes an amplifier and an amplifier controller according to an embodiment of the present invention.
Figure 12:
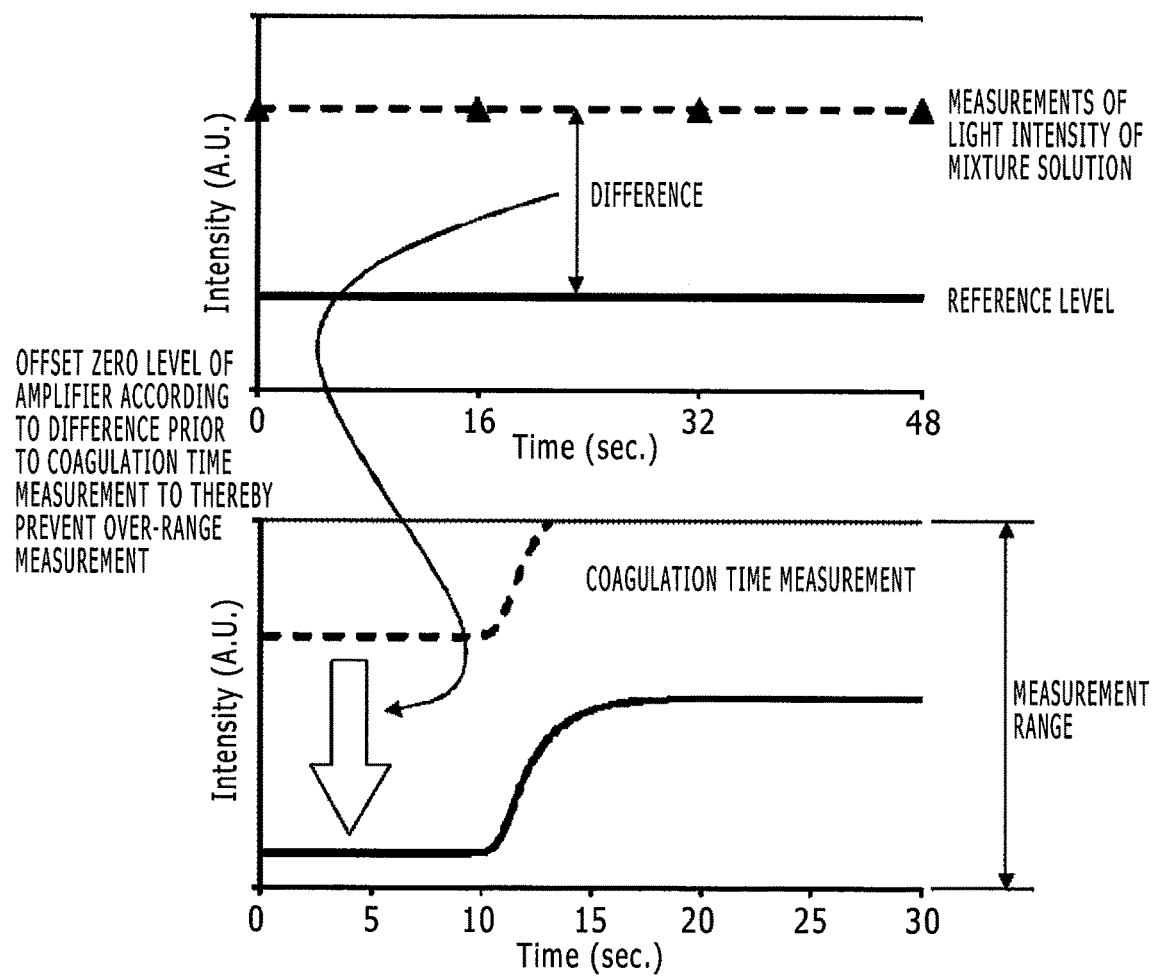
FIG. 12 is a diagram illustrating a zero level offset function for the amplifier according to the embodiment of the present invention.

Offset control of an amplifier may be performed with the use of this reference value. FIG. 11 shows this amplifier and an amplifier controller. The coagulation time detecting parts 61 include a detector, an amplifier 71, and an amplifier controller 72. The detector detects the transmitted light or the scattered light detected through the disposable reaction vessel. The amplifier 71 amplifies signals from the detector. The amplifier controller 72 controls the amplifier 71. The amplifier controller 72 acquires a reference value relating to the amount of interfering substance and, on the basis of the reference value, is capable of offsetting a zero level of the amplifier before the detector detects the light. FIG. 12 shows measurements of the photometer 41 (upper diagram) and measurements of the coagulation time detecting parts 61 (lower diagram). For example, the amplifier controller 72 may be controlled so that the zero level of the amplifier 71 that amplifies signals of the coagulation time detecting parts 61 is offset on the basis of a difference between the measurements of the transmitted light or the scattered light taken by the photometer 41 (the reference value relating to the amount of the interfering substance) and the predetermined reference level. This control makes it possible to achieve measurements with an appropriate amplification factor without involving inability of measurement due to an over-range measurement (FIGS. 11 and 12). This reduces frequency of events where the measurements being unable to be performed and achieves analyses with a minimum of waste of samples and reagents.

The correction and the zero level offset described above are also applicable to other analysis items that employ the same sample, because one measurement of the reference value can be used for other analysis items as long as the sample remains the same. The photometer 41 on the reaction disk side is not involved particularly in the analysis item associated with the single-reagent system, so that this photometer 41 cannot be used to directly measure the amount of the interfering substance. Preferably, therefore, corrections are made of measurement data taken from, among the samples used for other analysis items using the same sample, the sample with respect to the analysis items associated with the single-reagent system and the zero level is offset prior to the measurement.

Figure 9D:
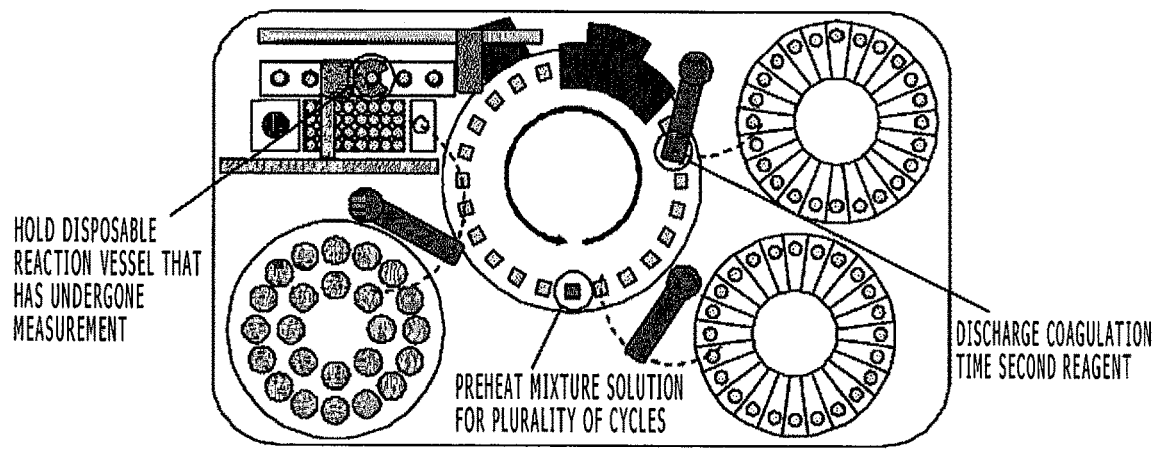
FIG. 9d is a diagram showing a general mechanical operation in blood coagulation time measurement (double-reagent system) according to the embodiment of the present invention.
Figure 9E:
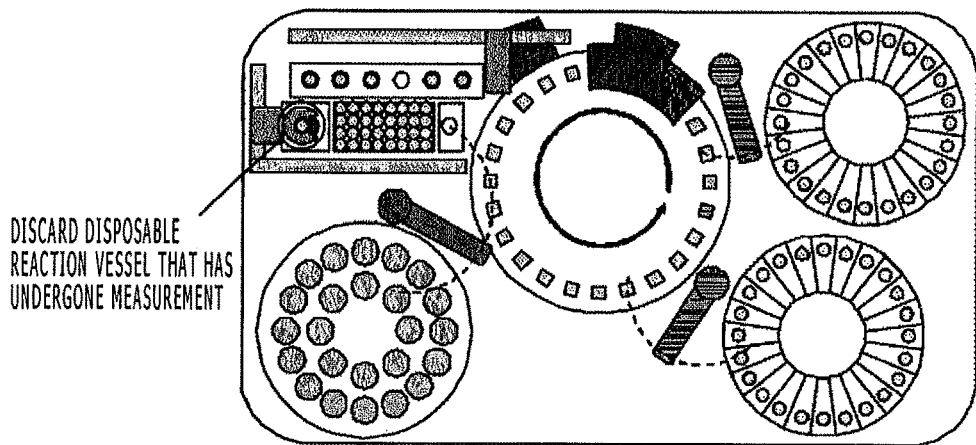
FIG. 9e is a diagram showing a general mechanical operation in blood coagulation time measurement (double-reagent system) according to the embodiment of the present invention.
Figure 9F:
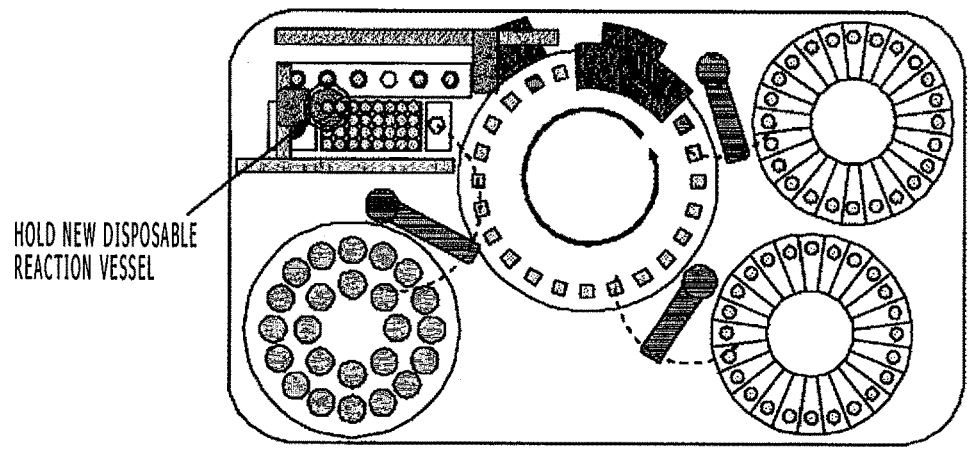
FIG. 9f is a diagram showing a general mechanical operation in blood coagulation time measurement (double-reagent system) according to the embodiment of the present invention.
Figure 9G:
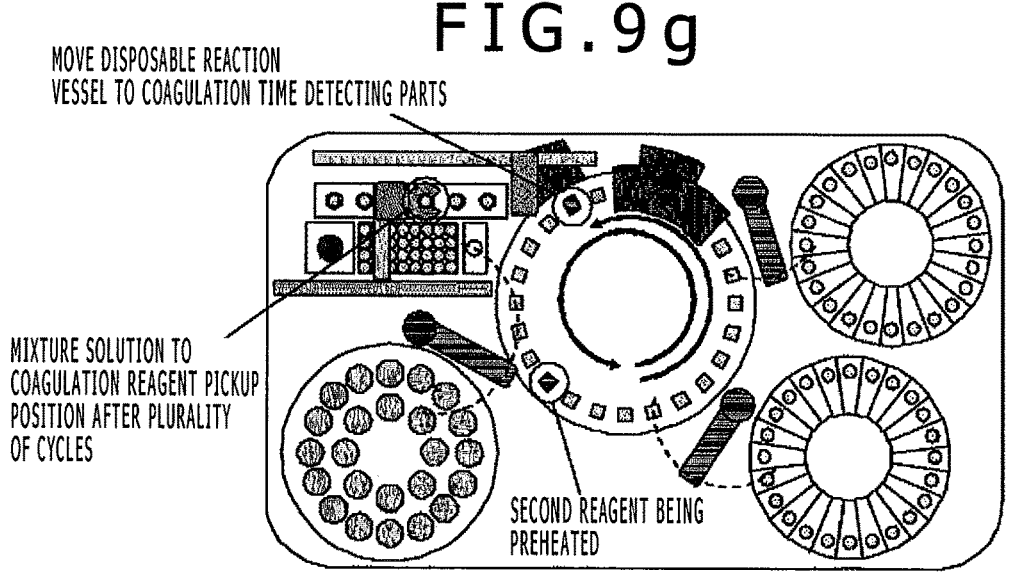
FIG. 9g is a diagram showing a general mechanical operation in blood coagulation time measurement (double-reagent system) according to the embodiment of the present invention.
Figure 9H:
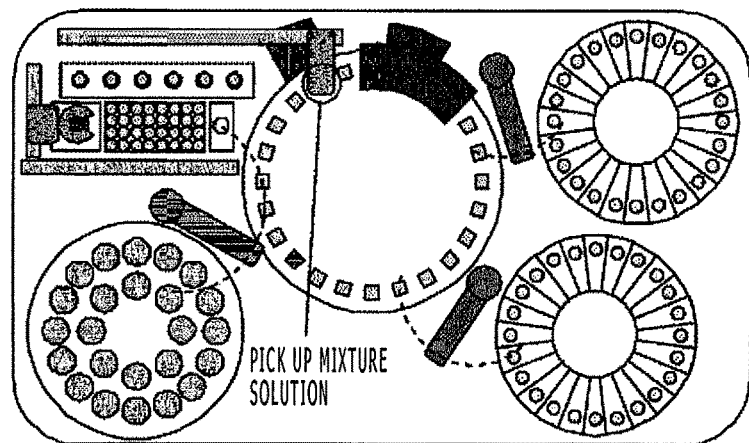
FIG. 9h is a diagram showing a general mechanical operation in blood coagulation time measurement (double-reagent system) according to the embodiment of the present invention.
Figure 9I:
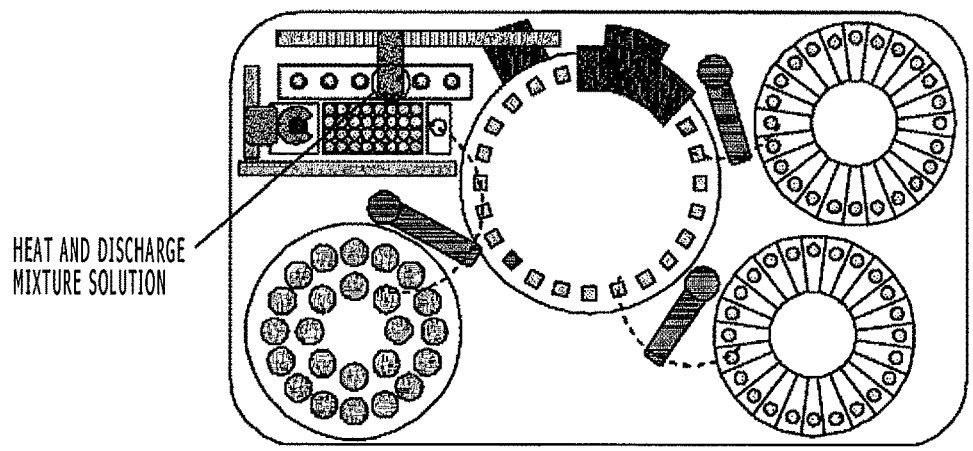
FIG. 9i is a diagram showing a general mechanical operation in blood coagulation time measurement (double-reagent system) according to the embodiment of the present invention.
Figure 9J:
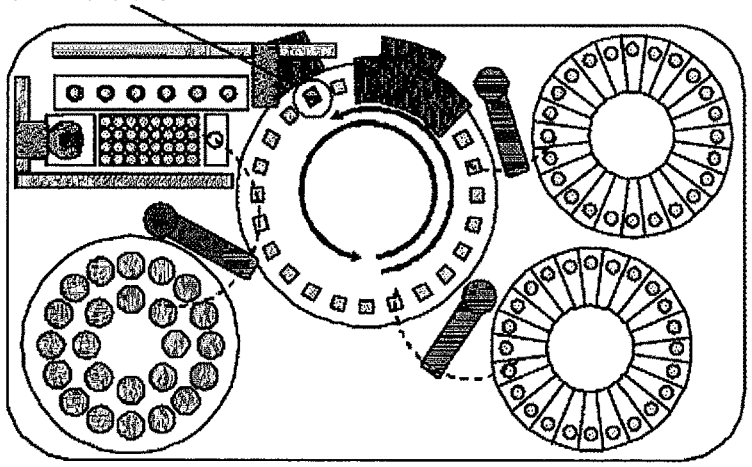
FIG. 9j is a diagram showing a general mechanical operation in blood coagulation time measurement (double-reagent system) according to the embodiment of the present invention.
Figure 9K:
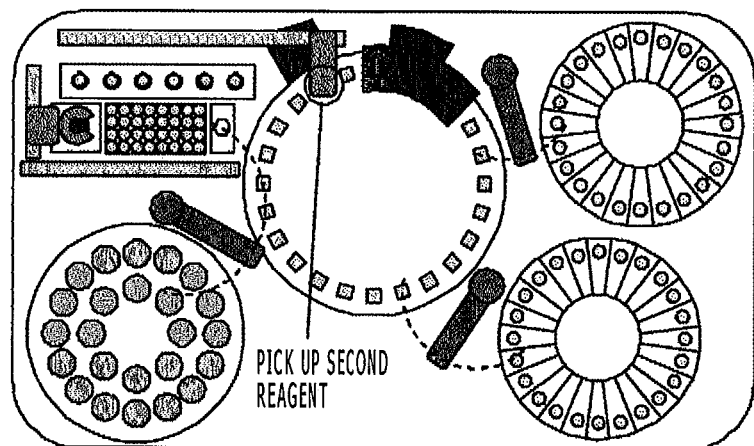
FIG. 9k is a diagram showing a general mechanical operation in blood coagulation time measurement (double-reagent system) according to the embodiment of the present invention.
Figure 9L:
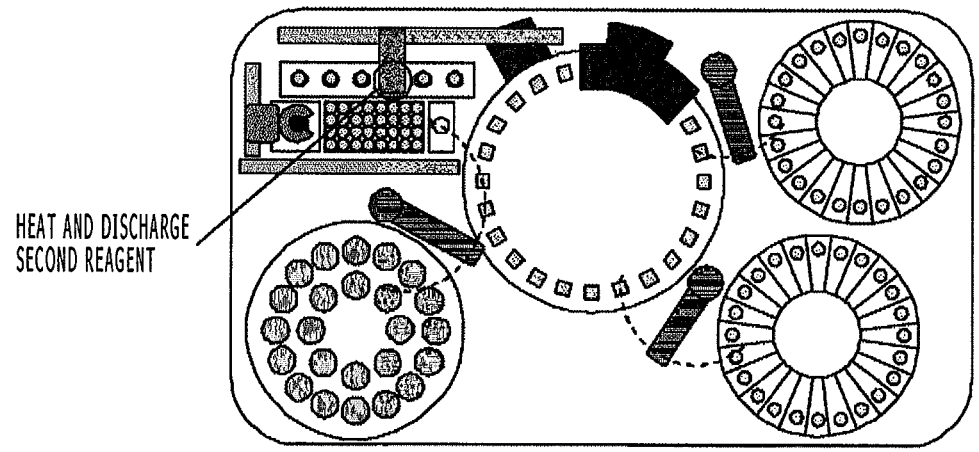
FIG. 9l is a diagram showing a general mechanical operation in blood coagulation time measurement (double-reagent system) according to the embodiment of the present invention.

Reference is made back to FIGS. 9a to 9l for the general operation. The reaction vessel transfer mechanism 65 discards the disposable reaction vessel 62 that has been subjected to the measurement in the reaction vessel discard section 67 (FIGS. 9d and 9e). The first reagent dispensing mechanism 34a discharges the second reagent at a predetermined timing into another reaction cell 11 different from the reaction cell 11 containing therein the mixture solution, the another reaction cell 11 being preheated to 37° C. on the reaction disk 10 (FIG. 9d). The reaction vessel transfer mechanism 65 holds a disposable reaction vessel 62 on the reaction vessel supply unit 63 (FIG. 9f) and moves the disposable reaction vessel 62 onto the coagulation time detecting parts 61 (FIG. 9g). The mixture solution that has been preheated is positioned at the blood coagulation reagent pickup position and sucked by the second reagent dispensing mechanism with a reagent heating function 66 (FIGS. 9g and 9h). The mixture solution, first heated by the second reagent dispensing mechanism with a reagent heating function 66 to a preset required temperature (e.g., 40° C.) so as to have a temperature of 37° C. at a timing immediately after it is discharged, is then discharged into the disposable reaction vessel 62 (FIG. 9i). The second reagent that has been preheated is thereafter positioned at the blood coagulation reagent pickup position and sucked by the second reagent dispensing mechanism with a reagent heating function 66 (FIGS. 9j and 9k). As with the mixture solution, the second reagent is first heated by the second reagent dispensing mechanism with a reagent heating function 66 to a preset required temperature (e.g., 40° C.) so as to have a temperature of 37° C. at a timing immediately after it is discharged and is then discharged into the disposable reaction vessel 62 (FIG. 9l). At this time, the mixture solution and the second reagent are agitated by means of a spurt of the second reagent being discharged and measurement of the blood coagulation time is started. The disposable reaction vessel 62 that has been subjected to the measurement is discarded by the reaction vessel transfer mechanism 65 into the reaction vessel discard section 67.

In coagulation time items exemplified by the thrombin reagent of the Fbg item, it is known that carry-over can affect subsequent measurements of coagulation time. Mounting a plurality of reagent dispensing mechanisms may be one of the solutions to the reagent carry-over problem; however, this involves complicated mechanisms with a resultant increase in system cost. The first reagent dispensing mechanism 34a and the second reagent dispensing mechanism with a reagent heating function 66 can be cleaned efficiently by the following procedure: specifically, the first reagent dispensing mechanism 34a sucks and discharges the cleaning agent into the reaction cell 11 in a cycle following the discharge of the reagent in the reaction cell 11, and the second reagent dispensing mechanism with a reagent heating function 66 sucks and discharges the cleaning agent in the reaction cell 11 in a cycle following the pickup and discharge of the preheated reagent. In addition, the cleaning agent used for the first reagent dispensing mechanism 34a is also used for cleaning the second reagent dispensing mechanism with a reagent heating function 66. This reduces consumption of the cleaning agent. Specifically, it is preferable in terms of reduction in the consumption of the cleaning agent that, depending on the item, the first reagent dispensing mechanism, after having discharged the reagent, pick up the cleaning agent and then discharge the previously-sucked cleaning agent into the reaction cell, and that the second reagent dispensing mechanism pick up the cleaning agent from the reaction cell into which the cleaning agent has been discharged and discharge the cleaning agent sucked earlier into a cleaning bath (not shown).

REFERENCE NUMERALS 1 automatic analyzer
10 reaction disk
11 reaction cell
12 constant-temperature bath
13 constant-temperature maintaining device
20 sample disk
21 sample vessel
22 sample dispensing mechanism
23 movable arm
24 pipette nozzle
30a first reagent disk
30b second reagent disk
31a first reagent refrigerator
31b second reagent refrigerator
32a first reagent bottles
32b second reagent bottles
33a first bar code reader
33b second bar code reader
34a first reagent dispensing mechanism
34b third reagent dispensing mechanism
35a first agitating mechanism
35b second agitating mechanism
36 reaction cell cleaning mechanism
40 light source
41 photometer
50 computer
51 interface
52 sample dispensing control unit
53 reagent dispensing control unit
54 A/D converter
55 printer
56 memory
57 external output medium
58 keyboard
59 CRT display (display device)
60 reaction vessel temperature-regulating block
61 coagulation time detecting part
62 disposable reaction vessel
63 reaction vessel supply unit
64 coagulation time sample dispensing position
65 reaction vessel transfer mechanism
66 second reagent dispensing mechanism with a reagent heating function
67 reaction vessel discard section
68 detecting section of heterogeneous immunoassay
69 B/F separating mechanism
70 disk of reagent of heterogeneous immunoassay
71 amplifier
72 amplifier controller

The invention claimed is:

1. An automatic analyzer, comprising:
a biochemical analyzer configured to perform biochemical analysis of a sample;
a blood coagulation time measuring section configured to analyze a blood coagulation time of the sample;
wherein the biochemical analyzer comprises:
a reaction disk on which a plurality of first reaction vessels are mounted;
a sample dispensing mechanism configured to dispense the sample to a first reaction vessel among the plurality of first reaction vessels;
a first reagent dispensing mechanism configured to dispense a first reagent or a diluent into the first reaction vessel; and
a first photometer configured to irradiate a first mixture solution contained in the first reaction vessel of the sample dispensed by the sample dispensing mechanism and the first reagent or the diluent dispensed by the first reagent dispensing mechanism, and to detect transmitted light or scattered light from the first mixture solution,
wherein the blood coagulation time measuring section comprises:
a second reagent dispensing mechanism configured to dispense the first mixture solution contained in the first reaction vessel, which has been subjected to transmitted light or scattered light detection by the first photometer, into a second reaction vessel disposed within a reaction vessel holder of the blood coagulation time measuring section from the first reaction vessel on the reaction disk, and to dispense a second reagent to the second reaction vessel containing the first mixture solution; and
a second photometer configured to irradiate a second mixture solution of the first mixture solution and the second reagent contained in the second reaction vessel, and to detect scattered light from the second mixture solution;
a controller; and
an amplifier, coupled to the controller, configured to amplify a signal acquired from the second photometer, and
wherein the controller is configured to:
acquire a value relating to an amount of an interfering substance contained in the sample included in the first mixture solution based on a detection result of the transmitted light or scattered light from the first mixture solution by the first photometer, and
control the amplifier to offset a zero level of the amplifier based on the value relating to the amount of the interfering substance before the measurement of the scattered light from the second mixture solution by the second photometer.

2. The automatic analyzer according to claim 1, wherein the controller is configured to correct a measurement result of the scattered light from the second mixture solution by the second photometer based on the value relating to the amount of the interfering substance.

3. The automatic analyzer according to claim 1, wherein the controller is configured to control the amplifier to offset the zero level of the amplifier based on a difference between the value relating to the amount of the interfering substance and a preset reference level.

4. The automatic analyzer according to claim 3, wherein the controller is configured to apply the offset to zero level of the amplifier to another analysis item using the sample.

5. The automatic analyzer according to claim 1, wherein the controller is configured to apply the correction to another analysis item using the sample.

6. The automatic analyzer according to claim 1,
wherein the controller is configured to apply the offset to zero level of the amplifier to another analysis item using the sample.

7. The automatic analyzer according to claim 1, further comprising:
a computer coupled to the biochemical analyzer and the blood coagulation time measuring section,
wherein the computer is configured to, when the controller and the second photometer of the blood coagulation time measuring section are conducting a measurement, start sample dispensation into the first reaction vessel by the sample dispensing mechanism based on either a time when a measurement end time of one of the coagulation time detecting parts is determined or a predetermined maximum measurement time.

* * * * *